United States Patent [19]

Van Aken et al.

[11] Patent Number: 5,319,437

[45] Date of Patent: Jun. 7, 1994

[54] HANDHELD PORTABLE SPECTROPHOTOMETER

[75] Inventors: Harold Van Aken, Wallkill; Alan Kravetz; Kenneth Garde, both of New Windsor; William Weber, Wallkill; Joseph Corrado, Newburgh, all of N.Y.

[73] Assignee: Kollmorgen Corporation, Simsbury, Conn.

[21] Appl. No.: 74,007

[22] Filed: Jun. 9, 1993

Related U.S. Application Data

[63] Continuation of Ser. No. 736,723, Jul. 26, 1991, abandoned.

[51] Int. Cl.$^5$ ............................ G01J 3/18; G01J 3/42
[52] U.S. Cl. ..................................... 356/326; 356/328
[58] Field of Search ............... 356/300, 319, 326, 328; 364/498, 526

[56] References Cited

U.S. PATENT DOCUMENTS

| | | |
|---|---|---|
| 2,882,786 | 11/1954 | Kaye . |
| 3,060,790 | 2/1959 | Ward . |
| 3,389,265 | 6/1968 | Schreckengust . |
| 3,519,834 | 7/1970 | Frederick . |
| 3,690,771 | 9/1972 | Armstrong, Jr. et al. ......... 250/226 |
| 3,776,642 | 12/1973 | Anson et al. ....................... 250/226 |
| 3,782,836 | 1/1974 | Fey et al. ........................... 356/237 |
| 3,885,878 | 5/1975 | Ishak ................................. 250/220 |
| 3,910,701 | 10/1975 | Henderson et al. .................. 356/39 |
| 3,916,168 | 10/1975 | McCarty et al. . |
| 3,923,899 | 12/1975 | Brumley ............................. 356/328 |
| 3,999,864 | 12/1976 | Mutter . |
| 4,029,419 | 6/1977 | Schumann, Jr. et al. ........... 250/226 |
| 4,076,421 | 2/1978 | Kishner . |
| 4,096,217 | 6/1978 | Roll . |
| 4,349,279 | 9/1982 | Jung ................................... 356/402 |
| 4,389,118 | 6/1983 | Yuasa et al. ....................... 356/404 |
| 4,449,821 | 5/1984 | Lee .................................... 356/319 |
| 4,469,441 | 9/1984 | Bernier et al. ..................... 356/316 |
| 4,479,718 | 10/1984 | Alman ............................... 356/405 |
| 4,552,458 | 11/1985 | Lowne ............................... 356/446 |
| 4,583,858 | 4/1986 | Lebling et al. ..................... 356/402 |
| 4,669,880 | 6/1987 | Nelson et al. ...................... 356/326 |
| 4,673,818 | 6/1987 | Guerra .............................. 250/571 |
| 4,711,580 | 12/1987 | Venable ............................. 356/406 |
| 4,773,761 | 9/1988 | Sugiyama et al. .................. 356/405 |
| 4,802,763 | 2/1989 | Gerlinger et al. .................. 356/319 |
| 4,853,879 | 8/1989 | Matzoll, Jr. et al. ............... 364/552 |
| 4,867,563 | 9/1989 | Wurm et al. ....................... 356/328 |
| 4,886,355 | 12/1989 | Keane .................................. 356/73 |
| 4,917,495 | 12/1990 | Steenhock .......................... 356/328 |
| 4,937,764 | 6/1990 | Komatsu et al. ................... 364/558 |
| 4,961,646 | 10/1990 | Schrämmli et al. ................ 356/328 |
| 5,073,029 | 12/1991 | Eberly et al. ........................ 356/39 |

FOREIGN PATENT DOCUMENTS 0079517 2/1982 European Pat. Off. .

(List continued on next page.)

OTHER PUBLICATIONS

G. Rosler, "Colormetric Characterization And Comparison Of Anisotropic Light Reflecting [Scattering] Samples", paper distributed Jun., 1988.

(List continued on next page.)

Primary Examiner—F. L. Evans
Attorney, Agent, or Firm—Morgan & Finnegan

[57] ABSTRACT

A handheld portable spectrophotometer is provided including keys for input of instructions by a user, an illuminator for illuminating a sample, and a spectral analyzer for separating light reflected from the sample into spectral components to produce a signal corresponding to the level of each spectral component. A processor is provided for executing the user instructions and for analyzing the signal. The results of the signal analysis are presented on a display. A power source is provided for providing power for operation of the handheld portable spectrophotometer.

59 Claims, 21 Drawing Sheets

FOREIGN PATENT DOCUMENTS

| | | |
|---|---|---|
| 0284811 | 3/1988 | European Pat. Off. . |
| 0375317 | 6/1990 | European Pat. Off. . |
| 0427220 | 5/1991 | European Pat. Off. . |
| 2101818 | 8/1971 | Fed. Rep. of Germany . |
| 3145633 | 8/1983 | Fed. Rep. of Germany . |
| 3315377 | 8/1984 | Fed. Rep. of Germany . |
| 8807666 | 9/1988 | Fed. Rep. of Germany . |
| 3843700 | 7/1990 | Fed. Rep. of Germany . |

OTHER PUBLICATIONS

Macbeth brochure for Color-Eye® 5010 Goniospectrophotometer, first sold May, 1988.

Gretag brochure for SPM 100 ™ Spectrophotometer, dated Jun. 1988.

Rodriques, "Total Instrumentation In Color Manufacture", Symposium On Color And Appearance Instrumentation, Mar. 16, 1978.

McCamy, "A Unified Approach To Appearance Measurement", Clemson University, Nov. 8, 1977.

Hunter UltraScan Spectrocolorimeter Brochure, undated.

X-Rite 418 Computerized Color Reflection Densitometer Brochure, undated.

Hunterlab MiniScan Brochure, undated.

X-Rite Graphic Arts Densitometers Brochure, undated.

Cosar Pressmate Densitometer Brochure, 1987.

Photocopy of Metron Handheld Spectrophotometer, undated.

FIG. 6C $\Delta L^*$    0.06  
$\Delta a^*$    10.21  
$\Delta b^*$    33.86  
$\Delta E$    35.37

TOLERANCES  
$\Delta L^x$    52.50    STAND20  
$\Delta a^x$    52.50  
$\Delta b^x$    52.50    ILL    D50  
$\Delta E$    52.50    OBS    2°

$L^x a^x b^x$    DIFF    ILL↑    DATA

FIG. 6D

TRIAL 1ST $L^*$    LIGHTER  
$a^*$    MORE RED  
$b^*$    MORE YELLOW $\Delta L^x$    0.06    STAND20    PASSED  
$\Delta a^x$    10.21  
$\Delta b^x$    33.86    ILL    D50  
$\Delta E$    35.37    OBS    2°

$L^x a^x b^x$    DIFF    ILL↑    ASMT

```
TRIAL IS:

L*   LIGHTER
        a*   MORE RED
        b*   MORE YELLOW

ΔL*   0.06   STAND20
  Δa*   10.21  PASSED
  Δb*   33.86  ILL    D50
  ΔE    35.37  OBS    2°
  STD↑  TRIAL  T SAVE  S
```

FIG. 6E

```
     AVERAGING:
      STD MODE
  TRIALS TO AVG.:  03
  COUNT:   [ 01 ]
            AVERAGE   LAST TRIAL
     L*     30.03     37.84
     a*      0.00      0.00
     b*     -0.00     -0.00

DROP              ACCEPT
```

FIG. 6F

```
     AVERAGING:
      SMC MODE

COUNT:   [ 06 ]
            MEAN     STD KEY
     L*    14.93      6.68
     a*     0.00      0.00
     b*    -0.00      0.00

TAKE NEXT MEASUREMENT
```

HANDHELD PORTABLE SPECTROPHOTOMETER

This is a continuation of co-pending application Ser. No. 07/736,723, filed on Jul. 26, 1991, now abandoned.

BACKGROUND OF THE INVENTION

This invention relates to spectrophotometers for the measurement of color and appearance of objects. More particularly, this invention relates to handheld portable spectrophotometers for remote measurement of color and appearance of objects.

Spectrophotometers are generally used to measure the color or appearance of objects, for example, paints, plastics, textiles, and to analyze powdered chemicals or biological specimens. Such color measurement may be used to formulate or adjust the mixture of colorants. Spectrophotometers measure the diffuse reflectance factor, which is defined as the ratio of light flux reflected from the sample to be measured to the light flux incident upon the sample and as compared with a "perfect white diffuser".

Most current spectrophotometers are tabletop instruments weighing in excess of 50 pounds and are generally connected to a personal computer for computation and analysis and operator control and display. The weight and size of the spectrophotometer results from the stability requirements of the internal optical system to maintain precise and consistent measurement of color. Operation of the spectrophotometer is also usually restricted to a limited range of operating temperature.

Accordingly, samples must be brought to the spectrophotometer to be measured for their color or appearance, necessitating, in some cases, taking a "swatch" or a piece of a very large object to a laboratory for color analysis. The computation complexity involved in the reformulation of colorants necessitates the use of a modern personal computer with the spectrophotometer for such analysis.

Some portable spectrophotometers have recently been developed but, while satisfying the portability requirement, such spectrophotometers fail to meet other important criteria. For example, temperature and mechanical shock sensitivity limit their ability to make accurate color measurements. Additionally, the computational power of such portable spectrophotometers is limited to mere measurement and display of color information with no analysis and correction of colorants, often referred to as "color matching". Color matching includes, by way of example, match prediction, batch corrections, tinting strength calculations, and retrieval of closest color shades from a shade library. Further, because of their box-like rectangular form, such portable spectrophotometers cannot access recessed or height-restricted environments such as the dashboard near the windshield of an automobile.

Accordingly, there exists a need for a portable spectrophotometer having the ability to access restricted environments and sufficient computational power for complex calculations of color measurement and colorant formulation.

SUMMARY OF THE INVENTION

In view of the foregoing, it is an object of the invention to provide a handheld portable spectrophotometer with the ability to perform measurements in restricted environments.

Another object of the invention is to provide a handheld portable spectrophotometer with the computational power to analyze and correct colorant formulations at a remote site.

Another object of the invention is to provide a handheld portable spectrophotometer having replaceable memory for interchanging data and software routines.

In accordance with a preferred embodiment of the invention, a handheld portable spectrophotometer is provided including keys for input of instructions by a user, an illuminator for illuminating a sample, and a spectral analyzer for separating light reflected from the sample into spectral components to produce a signal corresponding to the level of each spectral component. A processor is provided for executing the user instructions and for analyzing the signal. The results of the signal analysis including color matching and color formulation are presented on a display. A power source is provided for providing power for operation of the handheld portable spectrophotometer.

BRIEF DESCRIPTION OF THE DRAWINGS

The accompanying drawings, referred to herein and constituting a part hereof, illustrate a preferred embodiment of the invention and, together with the description, serve to explain the principles of the invention, wherein:

FIGS. 6A-6G are measure routine display screens displayed by the handheld portable spectrophotometer;

FIG. 10A-10E are data management routine display screens displayed by the handheld portable spectrophotometer;

FIGS. 12A-12G are setup routine display screens displayed by the handheld portable spectrophotometer;

DETAILED DESCRIPTION OF THE DRAWINGS

Figure 1A:
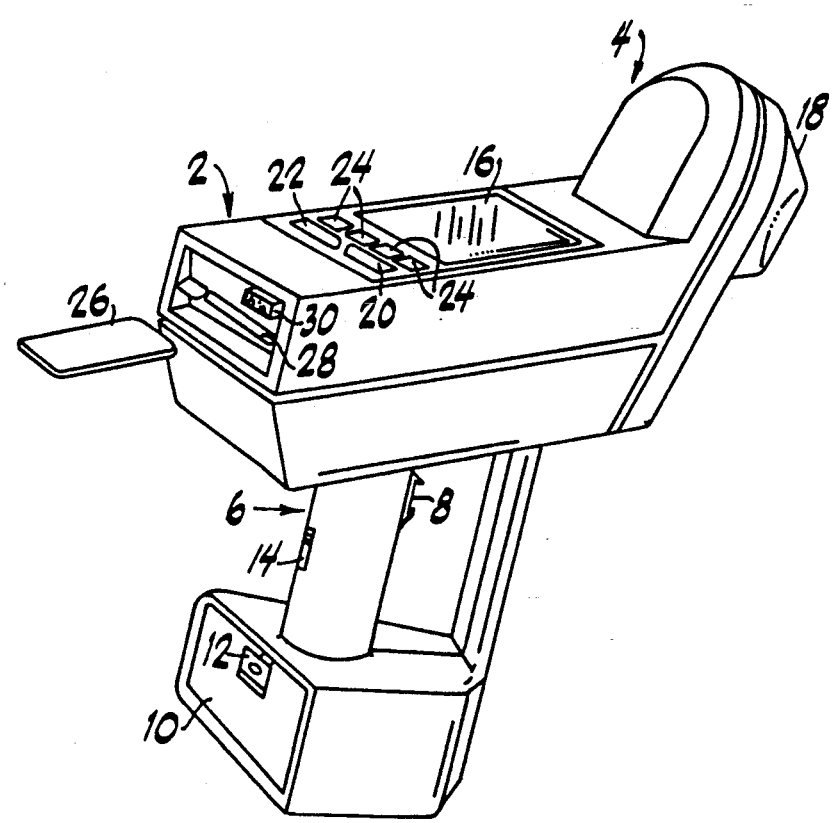
FIG. 1A is a perspective view of a handheld portable spectrophotometer in accordance with the invention.
Figure 1B:
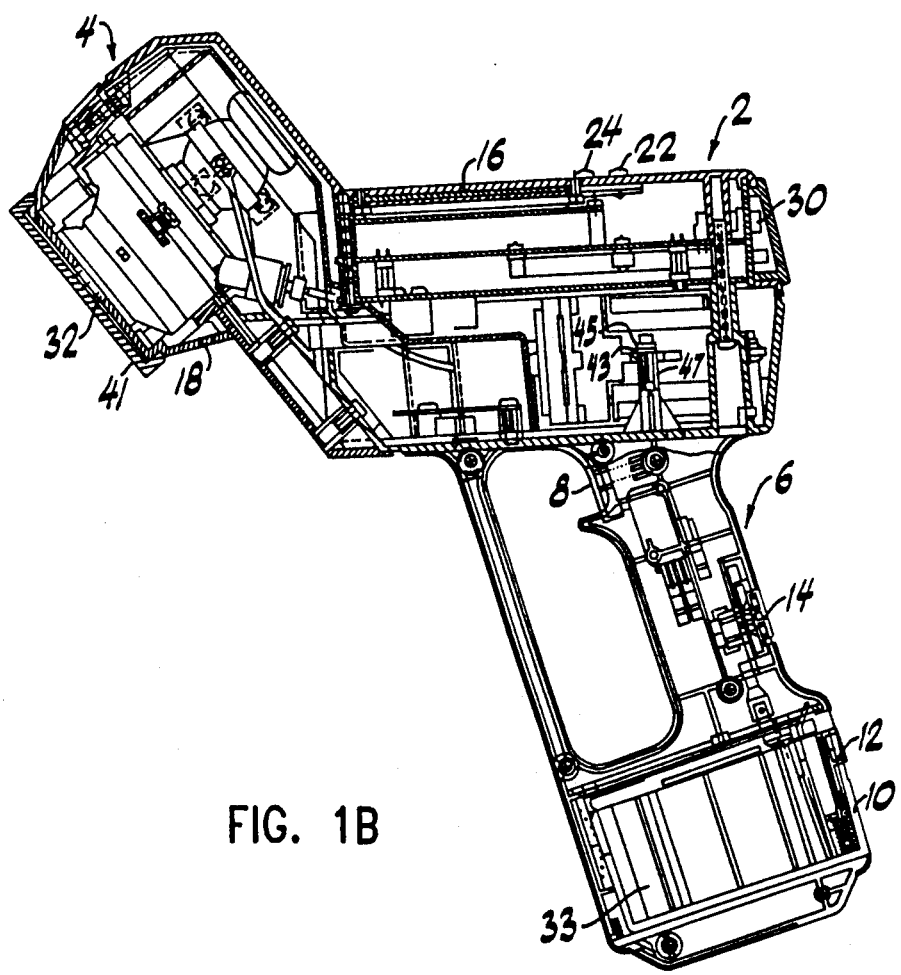
FIG. 1B is a side sectional view of the portable spectrophotometer.

FIG. 1A is a perspective view and FIG. 1B is a side sectional view of a handheld portable spectrophotometer in accordance with the instant invention. The portable spectrophotometer includes a body 2, an illuminator 4, and a handle 6. It may be appreciated from FIG. 1 the handle 6 is in a pistol grip configuration and the housing of illuminator 4 is non-coextensive with the housing of body 6 of the portable spectrophotometer. This non-coextensive arrangement of the housings of illuminator 4 and body 2 of the portable spectrophotometer is optimized for color measurement in restricted environments, such as in an automobile. The angle and shape of the housing of illuminator 4 allows color measurement of the dashboard even in areas close to the windshield. The protruding illuminator adaptor 18, having an aperture 32 therein, provides a point of contact between portable spectrophotometer and the target to be measured and also allows measurement of recessed areas and maximum visibility of the measured area.

The housings of the portable spectrophotometer are fabricated from an impact modified thermoplastic resin and is designed such that impact energy is readily absorbed in the housing structure. Multiple levels of housing interlocks allow for even stress distribution throughout the area of impact.

A suitable illuminator for use with the handheld portable spectrophotometer is disclosed in copending U.S. patent application Ser. No. 07/736,467 entitled APPARATUS AND METHOD FOR ILLUMINATING A SAMPLE. The disclosure of this patent application is incorporated herein in its entirety by reference.

Included as part of illuminator 4 are a xenon lamp and flash lamp circuitry. The xenon lamp is mounted in ultraviolet resistant silicon rubber "o" rings for maintaining lamp location while allowing some degree of vibration isolation.

The handle 6 of the portable spectrophotometer includes a trigger 8 which activates the flash lamp circuitry for illumination and measurement and may also be used (at appropriate points in the system operation) to scroll up and down through displayed information.

A battery compartment 10 which houses the battery pack power source is attached to handle 6 of the portable spectrophotometer. The battery release latch 12 unlocks the cover of the battery compartment 10 for access and service to the battery pack 33. The removable battery pack power source is 10 "C" size Nickel-Cadmium rechargeable cells. The capacity of the battery pack power source is sufficient for at least 1000 measurements and may be exchanged with a spare battery pack without interruption of operations. On the opposite side of the trigger is power switch 14 which applies and disconnects the power from the battery pack power source to the portable spectrophotometer. A power module converts the 12 volt battery voltage, by the use of switching supplies, to 5 volt logic, high voltage for the Xenon lamp, and 5 volt signal supplies.

The high voltage flash lamp power supply is a switched mode power supply that efficiently converts the battery voltage to the 320 volts needed by the xenon flash lamp. A Signetics SG3525 controller integrated circuit alternately turns on two field effect transistors that provide current to a step-up transformer whose output is configured as a voltage doubler. Two energy storage capacitors are charged and wait for the lamp to be triggered by a 6 kV pulse from the trigger transformer which is controlled by the microprocessor.

The voltage across the capacitors is fed back through a voltage divider to a comparator that compares it to an adjustable set point voltage. This integrated circuit turns on the power to the SG3525 controller integrated circuit and an "p amp" circuit that senses the transformer current. If this current reaches 4 amps another signal is applied to the SG3525 controller integrated circuit that shuts it off so that the magnetics of the transformer do not become saturated.

The body 2 of the portable spectrophotometer includes display screen 16, which is preferably an 128×128 LCD graphics display, for displaying menus and screens. The body 2 of the portable spectrophotometer also includes menu key 20, escape key 22 and software-controlled keys 24. The software-controlled keys 24 activate a variety of functions and are independently labeled depending on the particular screen display. The menu key 20 may also toggle the software-controlled keys 24 between primary and secondary menu functions. The escape key 22 returns the display screen 16 to a previously displayed screen or menu. The escape key 22 may also be used to access the display adjustment when the main menu is displayed.

The body 2 of the portable spectrophotometer is adapted to receive RAM card 26 which provides increased storage capacity and applications software packages. One such applications software package may be color matching which would provide match prediction, batch corrections, tinting strength calculations, and shade sorting. RAM card 26 fits into RAM card socket 28 which provides access to the RAM card by the portable spectrophotometer. Adjacent to the RAM card socket 28 is a DB9 connector 30 allowing connection of the portable spectrophotometer to a personnel computer or printer.

A suitable photodiode detector array and associated electronics for use with the handheld portable spectrophotometer is disclosed in copending U.S. patent application Ser. No. 07/736,721 entitled GAIN STABILIZED SELF-SCANNING PHOTO-DIODE ARRAY. The disclosure of this patent application is incorporated herein in its entirety by reference. For convenience, these components and their operation will also be described briefly herein.

Figure 2A:
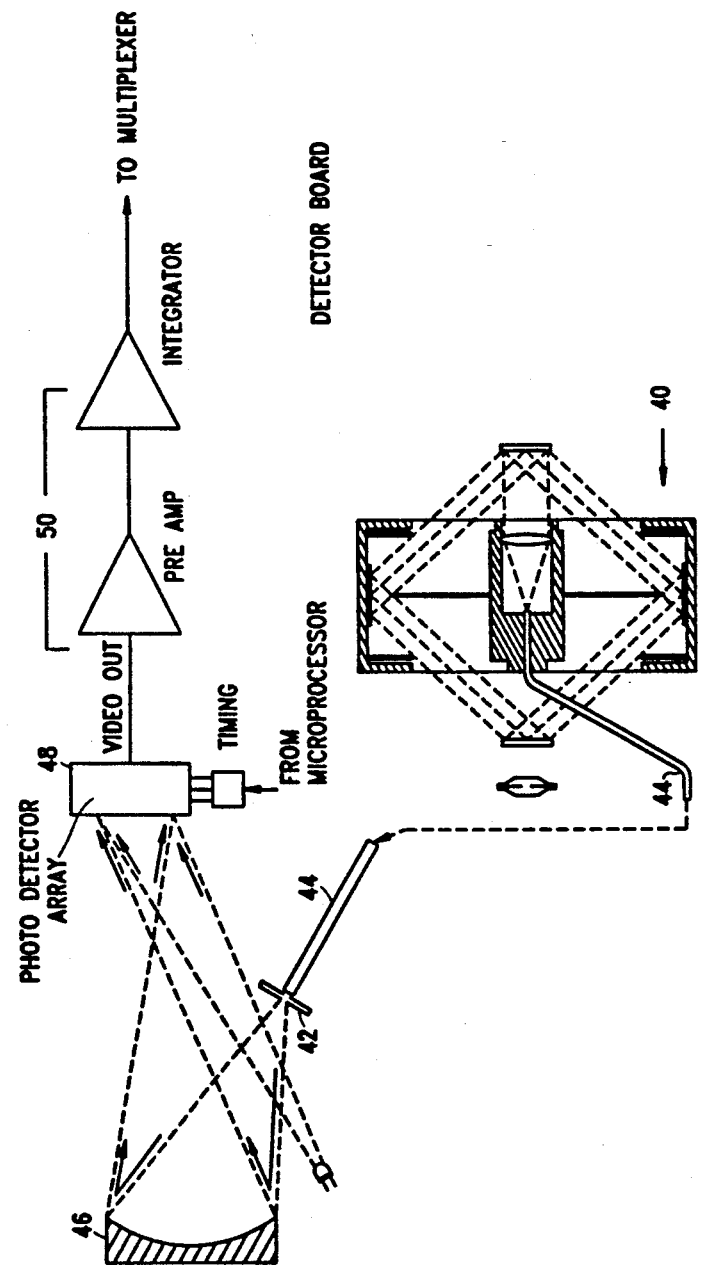
FIG. 2A is a schematic diagram of the spectral analyzer and illuminator of the handheld portable spectrophotometer.

FIG. 2A is a schematic diagram of the spectral analyzer and illuminator of the portable spectrophotometer. The spectral analyzer has a cast aluminum structure of a thermal design for mechanical stability over a wide range of operating temperatures. The slit 42 is illuminated by the acrylic optical fiber 44 from the illuminator module 40. The light passing through the slit is collected by a holographic grating 46 where the spectral components are separated and imaged simultaneously onto a 256-element silicon array 48 where the entire light pulse is integrated. At the end of the light pulse, each element of the array is shifted through an amplifier/integrator combination 50 providing a "video" stream of signals corresponding to the light level at each of the detector elements. All optical components in the spectral analyzer are bonded or glued with silicon rubber adhesive so that parts don't move.

Figure 2B:
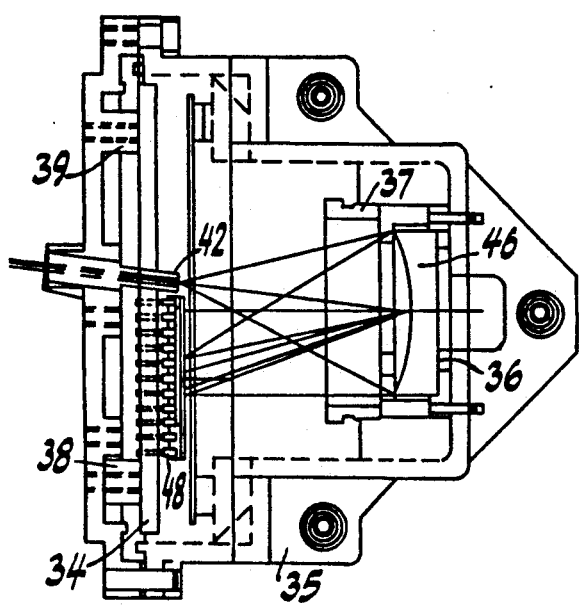
FIG. 2B is a top sectional view of the spectral analyzer of the handheld portable spectrophotometer.

As may be appreciated from FIGS. 1B and 2B, the spectral analyzer is supported by a three point mounting system. Each mount is comprised of an elastomer vibration dampener 43 and compression limiting bushing 45. This system allows the spectral analyzer to with stand a large spectrum of shock and vibration conditions. The analyzer is suspended on three hollow cantilever bosses 47 which act to dampen translational shear loads. Optical components inside the spectral analyzer are also bonded or glued in place and mounted such that the optical components maintain critical alignment even when subjected to extreme loads.

Figure 3A:
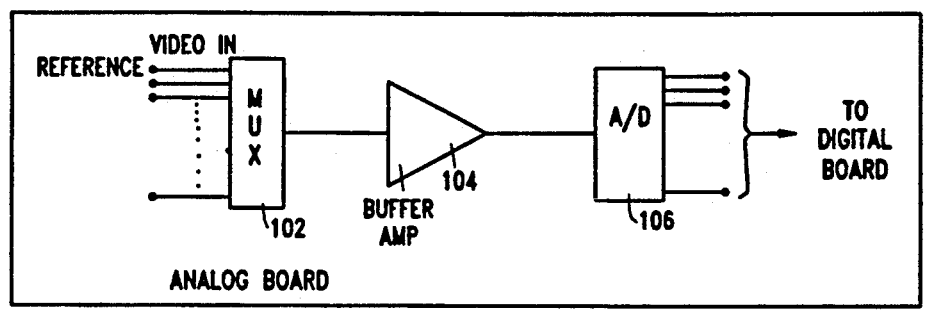
FIG. 3A is a schematic diagram of the analog board of the handheld portable spectrophotometer.

FIG. 3A shows the analog board of the portable spectrophotometer. The analog board includes multiplexer 102 coupled to a buffer amplifier 104. The output of the buffer is coupled to a 14 bit analog-to-digital (A/D) converter 106. The multiplexer selects one of the lines coupled to it, including the output of the spectral analyzer, and other analog information such as battery pack power indication, temperature, and reference channels. The output of the A/D converter 106 is coupled to an A/D buffer 116 as shown in FIG. 3B.

Figure 3B:
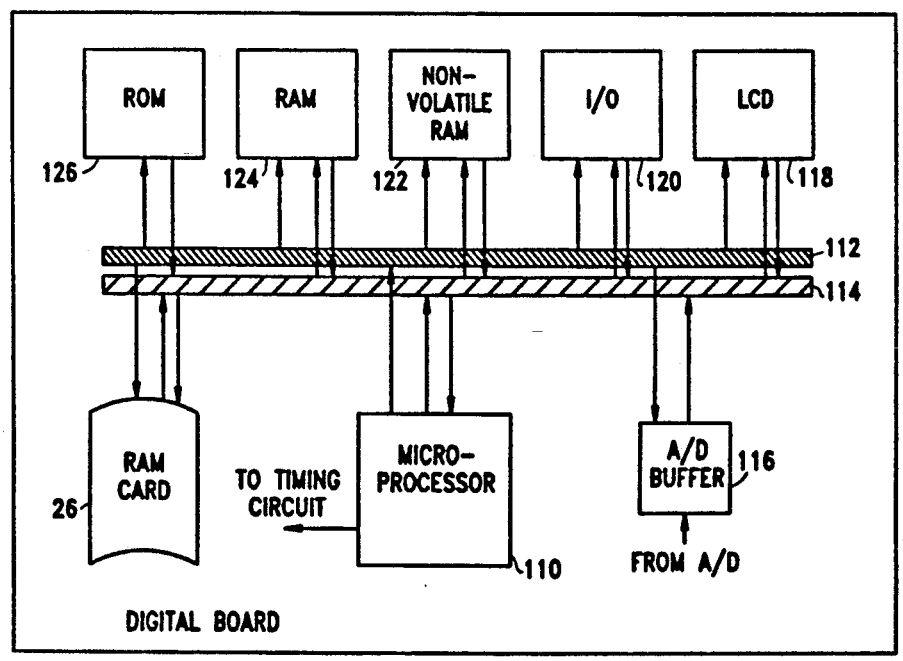
FIG. 3B is a schematic diagram of the digital board of the handheld portable spectrophotometer.

FIG. 3B shows the digital board of the portable spectrophotometer. The digital board includes a microprocessor 110. The microprocessor used in preferred embodiment of this invention is an Intel 80C188, which is a 16 bit microprocessor. The microprocessor is coupled to an address bus 112 and a data bus 114. Other components coupled to the address and data lines are A/D buffer 116, liquid crystal display (LCD) 118, keys (I/O) 120, non-volatile RAM 122, RAM 124, ROM 126 and RAM card 26.

A/D buffer 114 contains the digital signal generated by a 14 bit A/D converter 106. ROM 126 contains calibration information for a white standard, linearity coefficients for the detector array, wavelength calibration data for the spectral analyzer, and lamp calibration data for the xenon lamp. This information is provided as a reference for calibrating the spectrophotometer before actual use. RAM 124 is a scratch pad memory. RAM 124 contains information representing the output of the detector array after an illuminated sample reading and a non-illuminated sample reading, i.e., a dark reading. RAM 124 also contains coefficients generated upon calibrating the system with a white sample.

Non-volatile RAM 122, stores standard information of various colors. This information represents reference values against which the sample being analyzed is compared. RAM card 26 provides increased storage capacity and applications software packages. Information regarding color standards may be provided by the RAM card 26. LCD 118 and I/O 120 provide an interface with the user for selecting various functions of the portable spectrophotometer.

The spectral analyzer utilizes an a thermal design wherein the material selection and the techniques for mounting the optical components are such that changes in optical alignment due to temperature changes are largely corrected.

Referring to FIG. 2B, slit 42 illuminates holographic grating 46 with broadband illumination which is separated into spectral components and imaged onto detector array 48 that is mounted on a glass/epoxy printed circuit board 34. The grating 46 is attached to aluminum casting 35 at boss 36 and held in place with retaining ring 37 allowing movement on the other bosses. The printed circuit board 34 is bonded to boss 38 and is free to move horizontal on boss 39.

The aluminum casting 35 expands with temperature at the rate of 23 PPM per degree C which wouldn't be a problem if all parts were made of aluminum and expanded at the same rate. The printed circuit board 4 expands at 16 PPM causing an error for each 10 degrees C of a −0.3 nm if mounted at boss 39 or a +0.1 nm if mounted at boss 38. To compensate, the printed circuit board 34 is bonded to boss 32 and the holographic grating 46 is mounted off axis at boss 36 to correct the residual error to approximately 0.01 nm.

Accordingly, the spectral analyzer design significantly compensates for the thermal changes in the holographic grating 46 and the detector array 48. These components are mounted to avoid distortions caused by the differing thermal expansion rates of the different materials, and to control the effective common points of the components to the housing. In addition, the portable spectrophotometer housing material may be chosen to have high thermal conductivity to minimize thermal gradients.

The operation of these components of the portable spectrophotometer in taking a measurement may be briefly described as follows. A user-initiated instruction is issued by pressing the trigger 8. The instruction is directed as a switch closure signal through the microprocessor 110 which relays the signal to the flash lamp circuit. This causes the Xenon flash lamp to flash. The light from this flash enters an integrating chamber. The light then passes from the chamber out to a annular concave mirror which reflects the light through the aperture 32 in the illuminator 4.

The light exiting the illuminator illuminates the sample striking the sample at an angle of 45 degrees. A portion of this light is diffusely reflected onto the fold mirror collecting optics at an angle of zero degrees. The light collected is transmitted via a fiber optic bundle 44 to the spectral analyzer. The spectral analyzer includes a diffraction grating 46 that disperses the light collected into a spectrum and focuses it onto a detector array 48 to be measured. The signal from the detector array goes to the analog board and then to the digital board where it is processed and converted into a signal that is analyzed for display on the display screen 16.

The system control program required to control the operation of the portable spectrophotometer will be readily apparent to the skilled artisan based upon the description herein. Therefore, the following will not provide an unnecessarily lengthy description of the operation of such a program.

A. Main Menu

Figure 4:
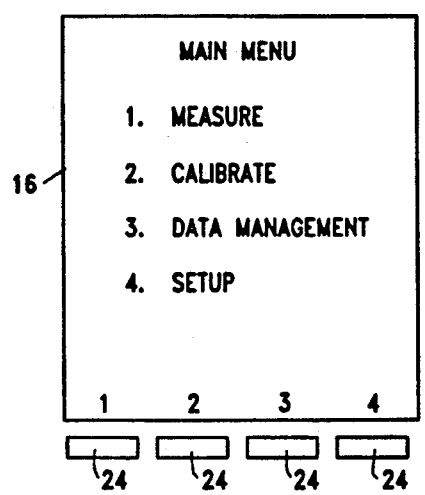
FIG. 4 is a main menu display screen displayed by the handheld portable spectrophotometer.

With the main menu displayed as shown in FIG. 4, the software-controlled key 24 labeled 1 (MEASURE) may be pressed to enter the measure mode and display data screens. This is usually done after the setup and calibrate routines. The software-controlled key 24 labeled 2 (CALIBRATE) may be pressed to access the calibration menu. This is usually done after the setup routine. The software-controlled key 24 labeled 3 (DATA MANAGEMENT) may be pressed to access the data management menu. The software-controlled key 24 labeled 4 (SETUP) may be pressed to access the setup menu. This is usually done first in order to customize the portable spectrophotometer to the specific needs of the user.

With the main menu displayed, the screen may be adjusted for optimum viewing by pressing and holding down the escape key 22 or pressing the menu key 20. The first two software-controlled keys 24 make the screen lighter. The second two software-controlled keys 24 make the screen darker. A level indicator may be displayed on the display screen 16 to show movement in either direction. The escape key 22 is released when the desired display level is obtained. This level will remain set until it is changed, even if the portable spectrophotometer is turned off and back on again.

B. Measure Routine

Prior to taking measurements with the portable spectrophotometer for the first time, the setup routine is performed. This routine allows configuration of the portable spectrophotometer with the color formulas and functions desired by the user. At the same time, this procedure allows deselection or turning off of those functions, illuminants, and color formulas that will not be used. By turning off the items that will not be used, the portable spectrophotometer's operation is simplified, since those items that will not be used do not appear on the display screen 16 during operation.

In order to ensure accurate measurement, regular calibration should be performed. For convenience, a transfer calibration tile may be provided in the illuminator adaptor protective cap 41.

Figure 5A:
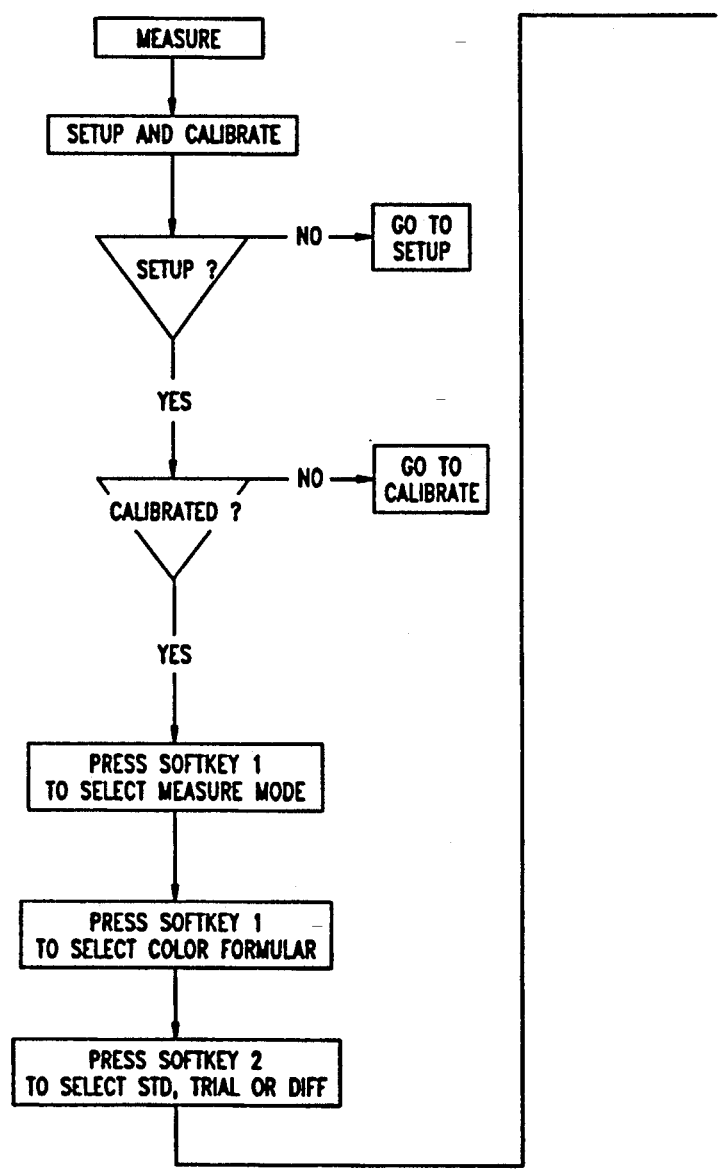
FIGS. 5A, 5A' and 5B are flow diagrams of the measure routine of the handheld portable spectrophotometer.
Figure 5A:
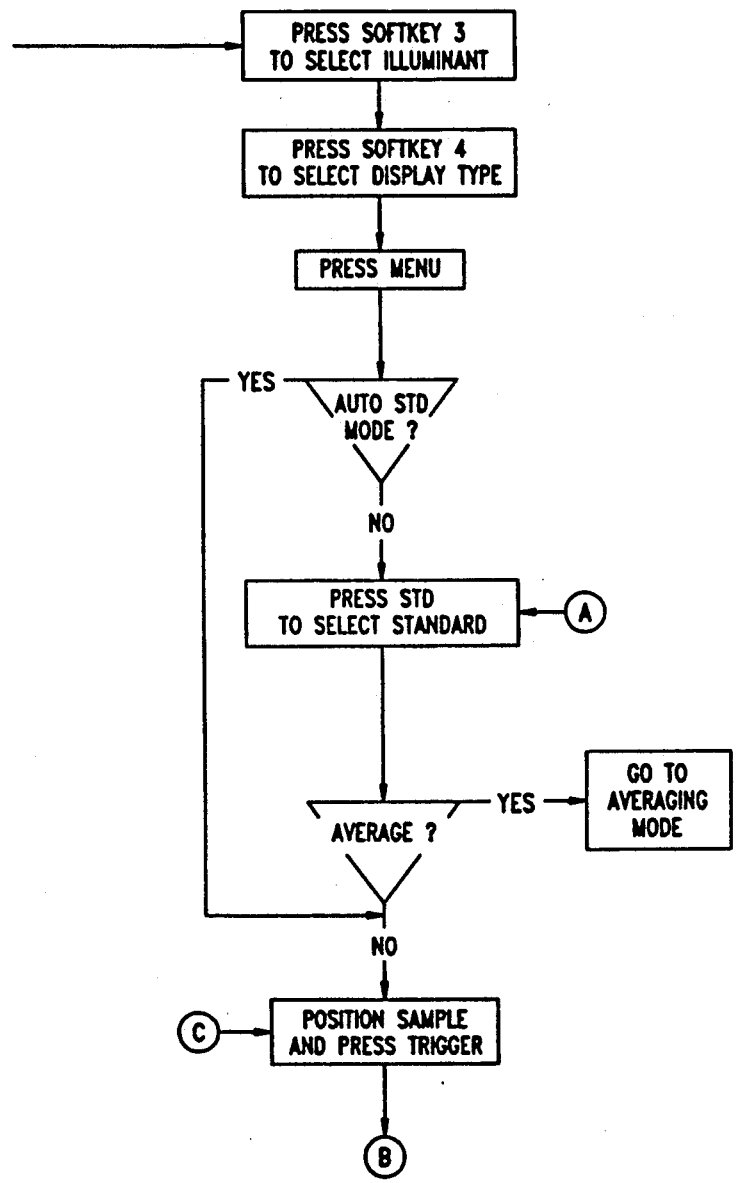
Figure 5B:
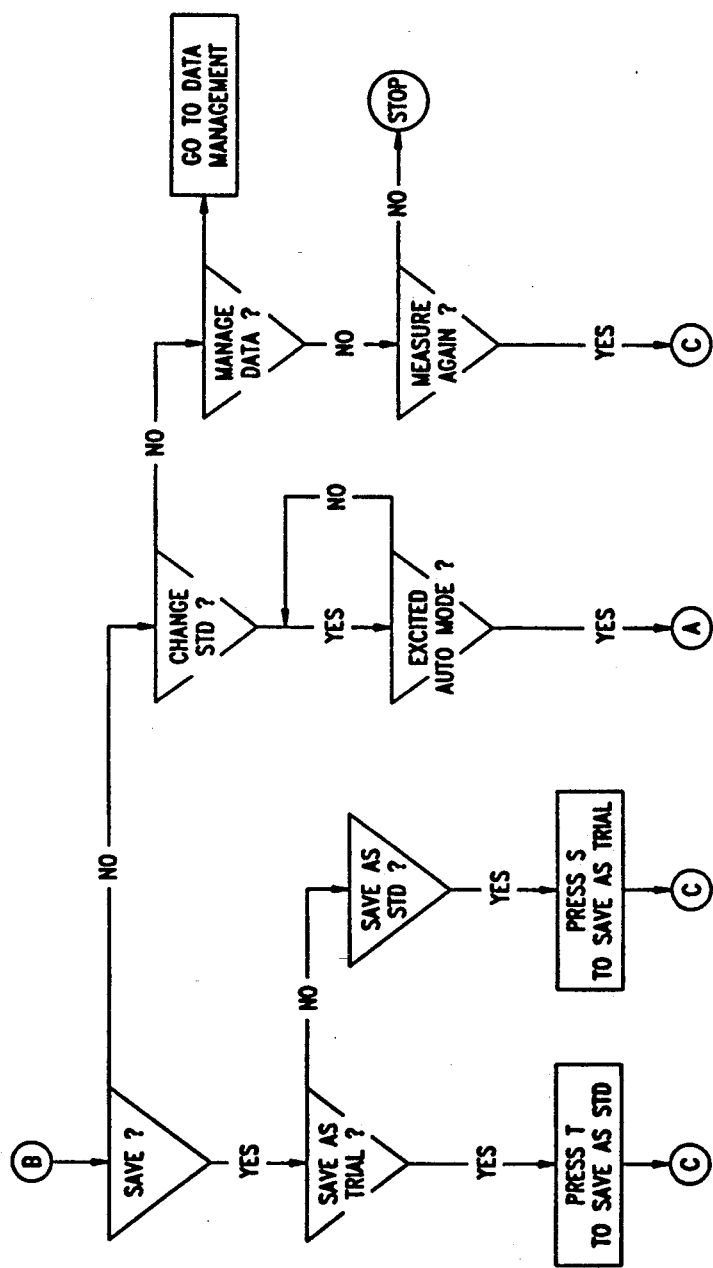
Figure 6B:
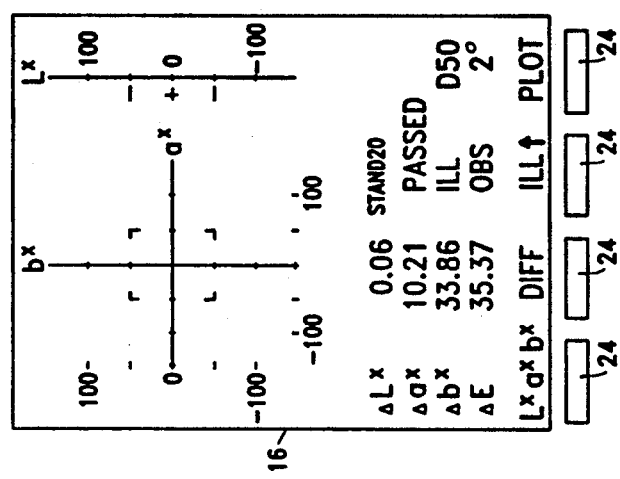
Figure 6A:
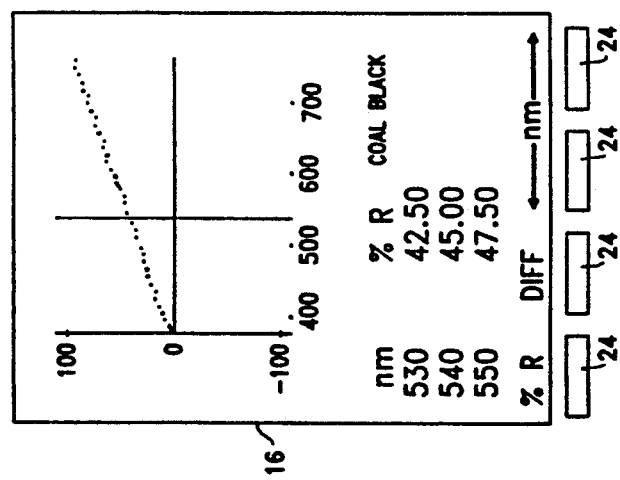

Once setup and calibration are completed, the portable spectrophotometer is ready to measure a sample. A flow diagram describing the measure routine of the portable spectrophotometer is set forth in FIG. 5A and 5B and is described hereinafter. For the sake of brevity, "software-controlled key labeled 1" is abbreviated as "SOFTKEY 1" in the flow diagrams. Similar notation is used for the other software-controlled keys in the flowcharts. To measure a sample, with the main menu displayed as shown in FIG. 4, software-controlled key 24 labeled 1 (MEASURE) is pressed. The portable spectrophotometer then displays the last trial measured in the same configuration chosen for that trial as shown in FIG. 6A. If the illuminator adapter 18 is pointed at a sample and the trigger 8 is pressed, data will be displayed on display screen 16 for a new trial in the same configuration displayed. As many measurements as desired may be repeated with this configuration displayed, or a different series of data configurations may be displayed.

To display the %R values for each of the nanometer intervals measured, the procedure is as follows. As illustrated in FIG. 6A, to get %R values less than those displayed, the software-controlled key 24 labeled left arrow (←) is pressed once allowing inspection of the numbers displayed under nm. The software-controlled key labeled left arrow (←) is pressed again if display of lower values is desired. Each time the software-controlled key labeled left arrow (←) is pressed, the selector cursor 32 moves to the left. To get %R values greater than those displayed, the software-controlled key 24 labeled right arrow (→) is pressed once, moving the selector cursor 32 to the right allowing inspection of the numbers displayed under nm. The software-controlled key labeled right arrow (→) is pressed again to display higher values.

Software-controlled key 24 labeled %R in FIG. 6A may be pressed to scroll through the color formulas that have been set up, stopping at the color formula to be displayed. L*a*b* is shown in FIG. 6B. Possible color formulas include %R, FMCII, L*a*b*, L*c*h*, and Lab. Software-controlled key 24 labeled DIFF in FIG. 6A may be pressed to select the color data to be displayed. Possible color data display options include standard, trial, and color difference. Software-controlled key 24 labeled ILL ↑ in FIG. 6B may be pressed to select the illuminant to be displayed. Possible illuminants include A, C, D50, D55, D65, D75, F2, F7 and F11. Software-controlled key 24 labeled PLOT in FIG. 6B is pressed to select the display mode. Possible display modes include plot, data, and assessment. The display mode shown in FIG. 6B is plot. A display screen in data display mode is shown in FIG. 6C. A display screen in assessment display mode is shown in FIG. 6D. Thereafter, the menu key 20 is pressed.

The portable spectrophotometer is now set up to measure and display data that the user wants to view. In order to proceed, however, it should first be determined which method is desired to collect trial data. The single measurement method is presented first, and the averaging measurement methods second.

The procedure for taking single measurements is as follows. The software-controlled key 24 labeled STD | as shown in FIG. 6E is pressed until the standard against which trial measurements is to be compared is displayed. If the portable spectrophotometer has been set up in auto standard mode, the standard will be selected after each measurement. This process is further explained below.

The illuminator 4 of the portable spectrophotometer is positioned over the trial sample to be measured making certain the illuminator adapter 18 is directly against the sample. Direct contact is important to accurate single measurements. The trigger 8 is pressed, the portable spectrophotometer takes a measurement, and the results are displayed on the display screen 16. To save the sample as a trial, the software-controlled key 24 labeled T is pressed.

Depending on how the save method in system setup was selected, the portable spectrophotometer saves trials and standards in one of the following four formats: APND being selected in setup results in the portable spectrophotometer adding the first 8 user-selected alphanumeric characters to the screen. These characters were specified after PREFIX: in the setup. TIME being selected in setup results in the portable spectrophotometer producing default names based upon a time/date stamp. The characters appear in a format similar to MMDDYY-HHMMSS where MM is the month, DD is the day, YY is the year, HH is the hour (based on a 24-hour clock), MM is the minute and SS is the second. STD being selected results in the portable spectrophotometer adding sequential numbers to the first eight characters of the active standard's name. FULL being selected results in the portable spectrophotometer displaying the editing screen. All alphanumeric characters may be manually entered.

To save the sample as a standard, the software-controlled key 24 labeled S is pressed. The previously described methods to save a trial also apply to saving a standard. To operate the portable spectrophotometer in auto standard mode, auto standard is turned on in system setup. A trial measurement is made by pressing the trigger (as previously described). In the auto standard mode, the standard that is closest to the trial is selected for the color difference comparison. This automatic sorting process chooses a standard based on the hue, value, and chroma of the trial. During the sort, the word AUTO blinks on the display screen. When the sort is complete, the name of the standard chosen appears directly above the passed or failed status line.

If the automatically-selected standard is not the one desired for use in comparison purposes, up to four additional standards for comparison may be selected. If the trial measurement is to be compared to the next closest standard to the one chosen, the menu key 20 is pressed. The software-controlled key labeled STD1 is pressed to view STD2 (the next closest standard). The softwarecontrolled key labeled STD2 is pressed again to go to STD3, and so forth up to STD5. Each time, the screen displays the new standard name and the color comparison for that standard.

To exit the auto mode the user must go to system setup and set auto standard to off. To do this, the escape key 22 is pressed to return to the main menu. Software-controlled key 24 labeled 4 (SETUP) is pressed. Software-controlled key 24 labeled 2 (SYSTEM SETUP) is then pressed. Auto standard may then be set to off.

There are two ways to set up the portable spectrophotometer for averaging measurements. The method chosen depends on the specific requirements for measurement precision. The user may determine whether the use of averaged measurements is needed for the specific application or if single measurements are adequate.

The first averaging method is simple averaging (standard mode). The number of measurements to take on each sample is specified. The portable spectrophotometer sequentially displays each measurement. The last measurement taken can be accepted or dropped. When the measurements are completed, the portable spectrophotometer displays the averaged result.

The second method of averaging is based on a confidence test (SMC mode). The differences between individual results are assessed. Based upon the standard deviation of the results, flyers are identified and eliminated from the averaging data set. Based on the formula chosen for SMC mode and the cutoff value assigned, the portable spectrophotometer determines an acceptable number of measurements required for good statistical precision of the averaged result.

The statistical measurement control (SMC) function is an averaging method that assists in taking the minimum number of readings necessary to ensure a reliable estimate of the true colorimetric value. The tests are performed in colorimetric data. Once sufficient readings have been taken to yield an acceptable result, reflectance values for the selected data are averaged and used to calculate the final colorimetric values. The SMC function requires from 5 to 50 readings per sample. The acceptable number of sample readings that are required for this assessment various depending on the extent of sample nonuniformity, sample positioning accuracy, and within-instrument repeatability.

The technique requires an initial flyer or outlier test on the data set in order to eliminate totally nonconforming measurements. The mean ($\bar{x}$), and standard deviation (s) of this test are modified each time a measurement is taken, by comparing the new value to a cutoff value that has been calculated for the total number of (N) measurements examined. This cycle is repeated until the modified standard deviation is within an acceptable user-defined tolerance. Each time new readings are taken, data from all previously identified flyers are retested with the new data points.

The method used in statistical measurement control is derived from Cloppenburg, H. and Schmittman, D., "Farbmessungen an Metalliclacken", 1989, 95 *Farb-+Lack*, pp. 631–6:

1. Take 5 measurements
2. Calculate the mean ($\bar{x}$), and standard deviation for these values.
3. Use the following TEST argument on each individual measurement.

$$x_i - \bar{x} > 2.5s$$

where $x_i$ is the individual test measurement, $\bar{x}$ is the mean of the measured values, and s is the standard deviation based on N total measurements.

4. If the calculated value is greater than 2.5 times the standard deviation, then the individual test measurement ($x_i$) is discarded.
5. Repeat this process for all remaining values. Once flyers have been eliminated, make certain that there are at least 5 measurements remaining and proceed to step 6.
6. Divide the standard deviation of the remaining measurements by the square root of the number of remaining measurements. Test this value to determine if it is less than the cutoff value entered by the user (the average error of the measurements included in the average). If this value is less than the cutoff (entered on the system setup screen as the SMC cutoff), accept the average as an accurate reading. If the value is not acceptable, another measurement must be made and repeat the entire process with all flyers reinstated into the group of measurements.

To make measurements in the STD mode, this option is chosen in the system setup as described previously. Std avg #recs is set to the number of measurements to be averaged. The escape key 22 is pressed to return to the main menu. Software-controlled key 24 labeled 1 (MEASURE) is pressed. The trigger 8 is pressed to make the first measurement. As illustrated in FIG. 6F, the display screen 16 displays the number of trials to average and the count number of the measurement that has just been made. The screen also displays the color difference values for the measurement. The software-controlled key 24 labeled DROP may be pressed to reject a result. The software-controlled key 24 labeled ACCEPT may be pressed when a result is to be included in the average, but immediately exit averaging this sample. This procedure is repeated until all the measurements are complete.

The display screen 16 displays the averaged result in the mode selected. If the %R mode is selected, the display screen 16 displays a spectral curve of each measurement. Color values displayed (e.g., L*, a*, and b*) change depending on the screen from which the user begins.

To make measurements in SMC mode, this option is chosen in system setup as described previously. Based upon the cutoff specified in system setup, the portable spectrophotometer determines the number of measurements to average. This number ranges from 5 to 50 measurements. From the main menu, softwarecontrolled key 24 labeled 1 (MEASURE) is pressed. The trigger 8 is pressed to make the first measurement. As illustrated in FIG. 6G, the display screen 16 displays the count number of the measurement that has just been made. The display screen 16 also displays the color difference values for the measurement. The trigger 8 is pressed to make the next measurement, and this procedure is repeated until the display screen 16 displays the SMC averaged result.

C. Calibrate Routine

Figure 7:
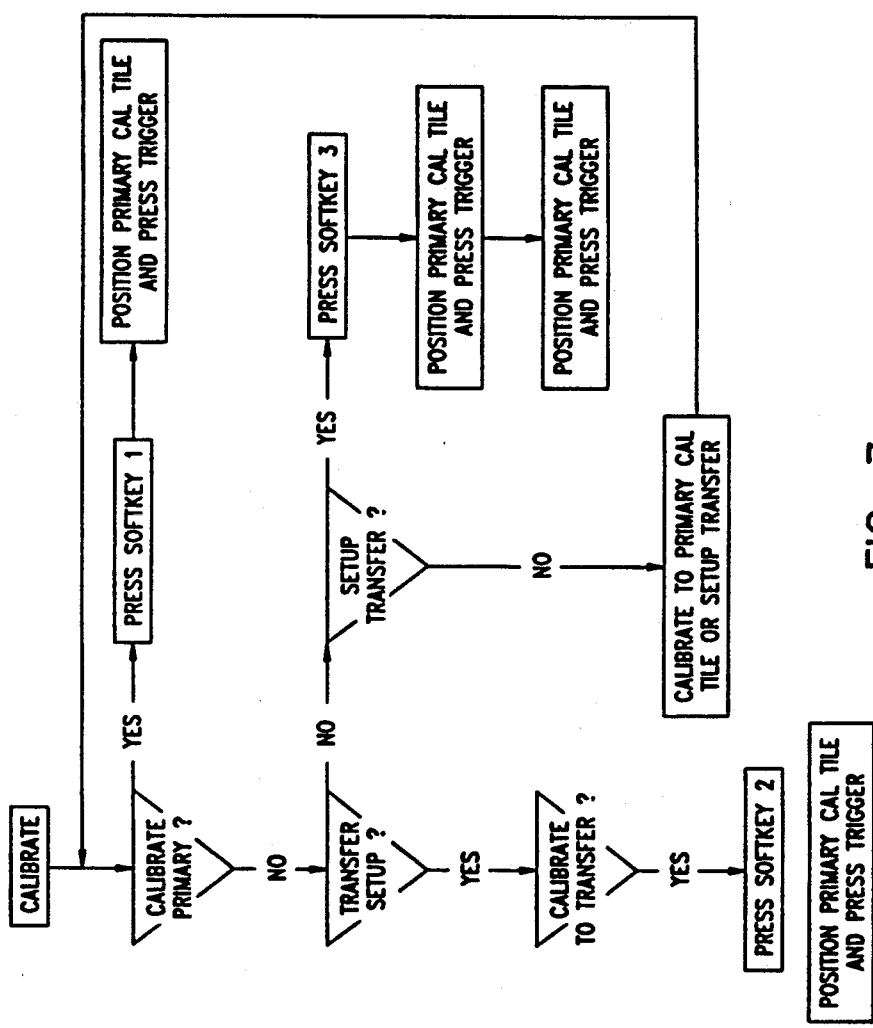
FIG. 7 is a flow diagram of the calibrate routine of the handheld portable spectrophotometer.
Figure 8:
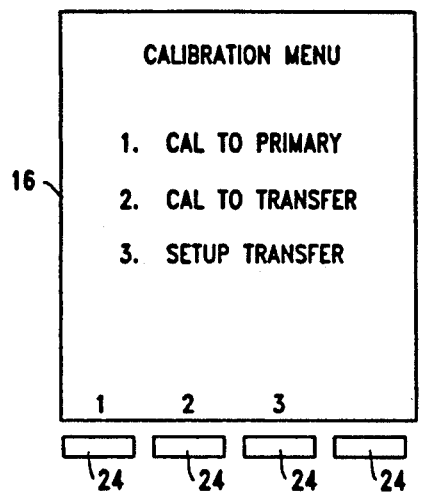
FIG. 8 is a calibrate routine display screen displayed by the handheld portable spectrophotometer.

A flow diagram describing the calibrate routine of the portable spectrophotometer is set forth in FIG. 7 and described hereinafter. In order facilitate checking the calibration of the portable spectrophotometer, a secondary or transfer calibration tile may be provided in the protective cap 41 to the illuminator adaptor 18. This allows the user to recalibrate to either the primary or transfer tiles. To calibrate, with the main menu displayed, software-controlled key 24 labeled 2 (CALIBRATE) is pressed to display the calibration menu as illustrated in FIG. 8. With the calibration menu displayed, software-controlled key 24 labeled 1 (CAL TO PRIMARY) is pressed to calibrate the portable spectrophotometer to the white primary calibration tile or software-controlled key 24 labeled 2 (CAL TO TRANSFER) is pressed to calibrate the portable spectrophotometer to the transfer calibration tile located in the illuminator adapter protective cap 41. Software-controlled key 24 labeled 3 (SET UP TRANSFER) may be pressed to set up the transfer calibration tile. It is advisable to set up the transfer tile and calibrate to it periodically throughout the measurement procedure. It is also possible to calibrate to the white primary calibration tile and to use this calibration for measurements. Additionally, the user may recalibrate to the primary calibration tile.

To calibrate to the primary calibration tile, software-controlled key 24 labeled 1 (CAL TO PRIMARY) is pressed. The white primary calibration tile is removed from its protective holder and, placed in the hand opposite the one holding the portable spectrophotometer. The tile is aligned flat against the illuminator adapter 18 and the trigger 8 is pressed. The display screen 16 displays CALIBRATED TO PRIMARY.

To set up the transfer calibration tile, softwarecontrolled key 24 labeled 3 (SET UP TRANSFER) is pressed. The white primary calibration tile is removed from its protective holder and placed in the hand opposite the one holding the portable spectrophotometer. The tile is aligned flat against the illuminator adapter and the trigger is pressed. The illuminator protective cap 41 containing the transfer calibration tile is placed on the portable spectrophotometer. The trigger 8 is pressed and the display screen 16 displays TRANSFER CALCIBRATION IS SET UP.

To calibrate to the transfer calibration tile, software-controlled key 24 labeled 2 (CAL TO TRANSFER) is pressed. The protective cap 41 containing the transfer calibration tile is placed on the portable spectrophotometer and the trigger 8 is pressed. The display screen 16 displays CALIBRATED TO TRANSFER.

D. Data Management Routine

Figure 9A:
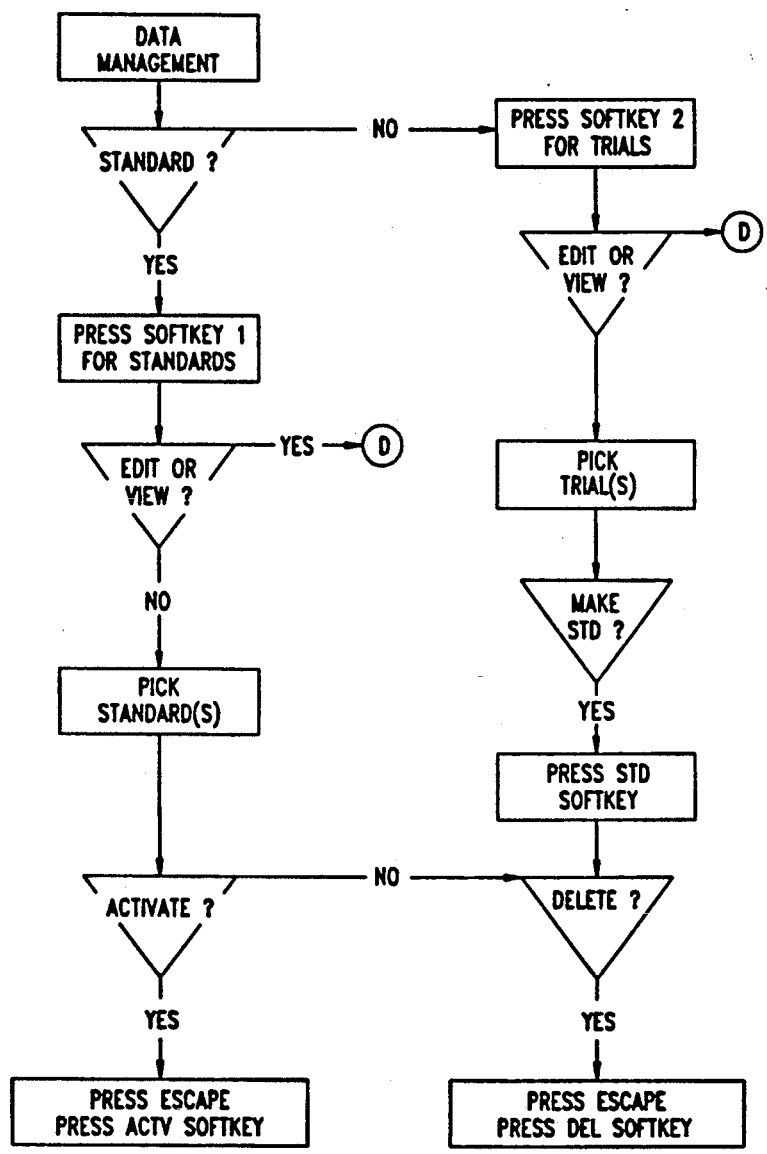
FIGS. 9A and 9B are flow diagrams of the data management routine of the handheld portable spectrophotometer.
Figure 9B:
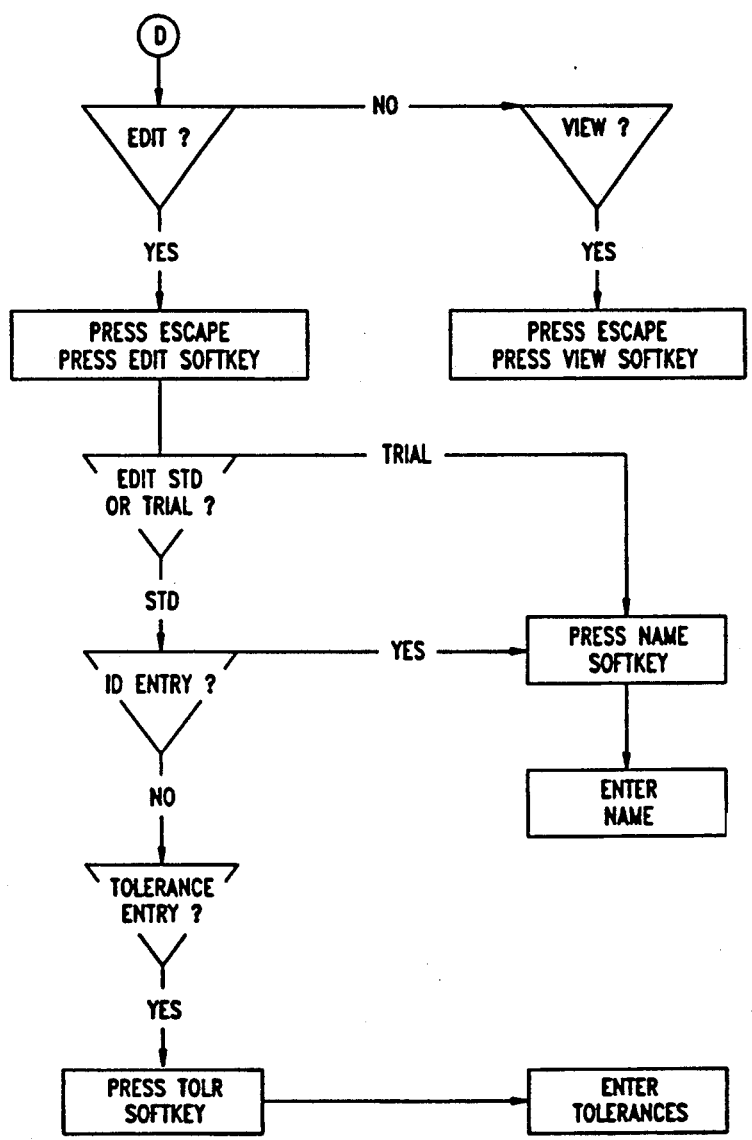

A flow diagram describing the data management routine of the portable spectrophotometer is set forth in FIG. 9 and described hereinafter. Data may be managed for standards or trials residing within the portable spectrophotometer's memory or on a RAM card. The portable spectrophotometer has the capacity to store up to 250 standards and trials. This number may be expanded by use of a RAM card 26 that operates in the data storage mode. With a RAM card 26 in place, the portable spectrophotometer can store many additional standards and trials. The number of standards and trials is only limited by the memory available on the RAM card 26. On startup, the portable spectrophotometer immediately recognizes the presence of the RAM card 26 and determines whether the card is used for data storage or a specific application.

Data management may also be accomplished using personal computer software adapted for use with the portable spectrophotometer. The use of the portable spectrophotometer in conjunction with a personal computer is described more fully below.

Figure 10A:
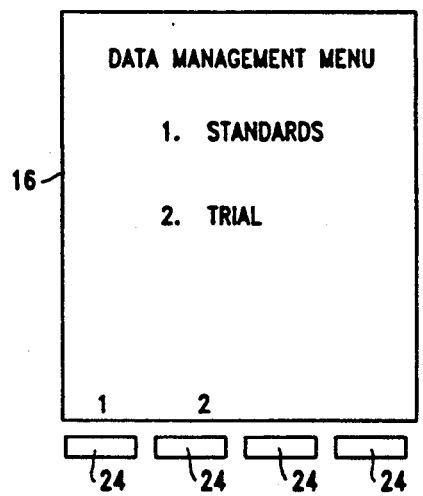
Figure 10B:
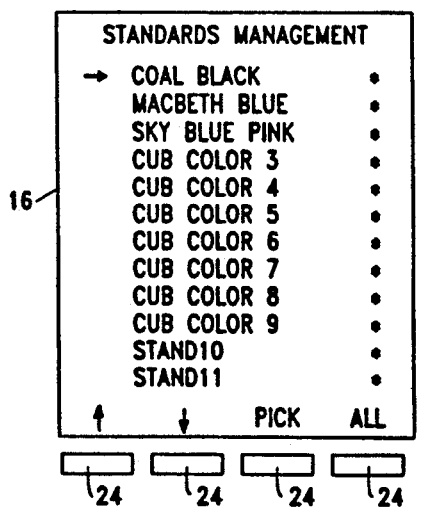

When software-controlled key 24 labeled 3 (DATA MANAGEMENT) is selected from the main menu, either standards or trials may be modified. By selecting software-controlled key 24 labeled 1 (STANDARDS) or 2 (TRIAL) from the data management menu illustrated in FIG. 10A, the currently stored data for each is displayed. An asterisk (*) placed to the right of a standard's name, as shown in FIG. 10B, indicates that this standard is active. This means that in measure mode, all standards marked with an asterisk in data management are active, and available for manual or auto selection operations. If many standards or trials are stored, screens may be scrolled through by pressing the trigger 8 and either software-controlled key 24 labeled up arrow (↑) to move up the list or software-controlled key 24 labeled down arrow (↓) to move down the list a screen at a time.

For standards data management, with the main menu displayed as shown in FIG. 4, software-controlled key 24 labeled 3 (DATA MANAGEMENT) is pressed. With the data management menu displayed as shown in FIG. 10A, software-controlled key 24 labeled 1 (STANDARDS) is pressed to enter the standards data management mode; or software-controlled key 24 labeled 2 (TRIAL) is pressed to enter the trial data management mode.

To access standards data management, with the data management menu displayed, software-controlled key 24 labeled 1 (STANDARDS) is pressed. Once standards have been saved, they may be viewed or edited. To edit or view a standard, an individual standard is selected by pressing the software-controlled key 24 labeled up arrow (↑) or the software-controlled key 24 labeled down arrow (↓) as shown in FIG. 10B to move the selector arrow 34 adjacent to the standard to be edited or viewed. To view the standard selected, the menu key 20 is pressed to obtain the screen display shown in FIG. 10C. The software-controlled key 24 labeled VIEW is then pressed to display the standard chosen. The escape key 22 is pressed to return to the standards management menu. To edit the standard selected, the menu key 20 is pressed to obtain the screen display shown in FIG. 10C and then the software-controlled key 24 labeled EDIT is pressed. The standard's name or its tolerance may be edited as described below.

To edit the standard's name, the software-controlled key 24 labeled NAME is pressed. The same procedure is used to edit the name as the one described in system setup using the display screen shown in FIG. 10D.

Figure 10C:
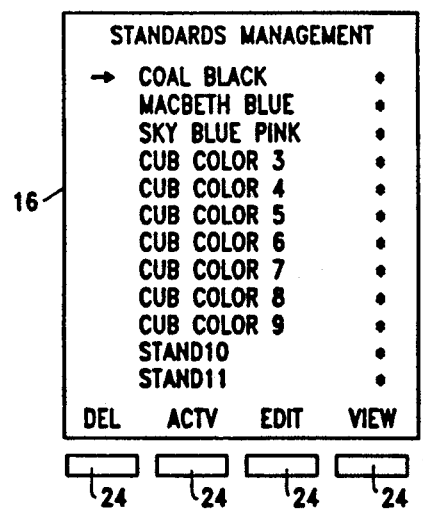
Figures 10D, 10E, 12A, 12B:
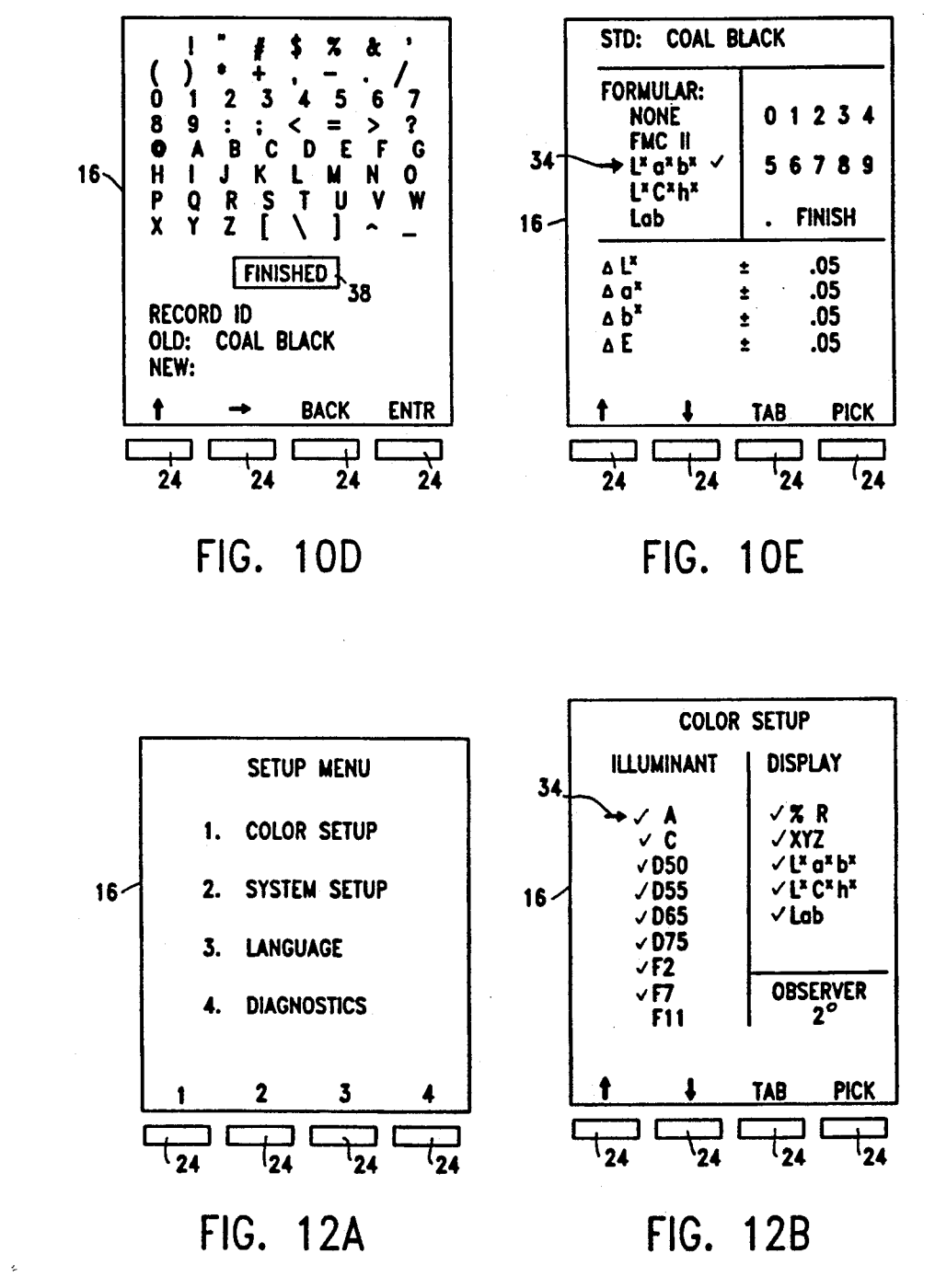

To edit the standard's tolerance, with the primary standards management menu displayed as shown in FIG. 10B, the menu key 20 is pressed. With the secondary standards management menu displayed as shown in FIG. 10C, the software-controlled key 24 labeled EDIT is pressed. Then, the software-controlled key 24 labeled TOLR is pressed. The color formula for which tolerances are to be entered is chosen by pressing the software-controlled key 24 labeled up arrow (↑) or the software-controlled key 24 labeled down arrow (↓) as shown in FIG. 10E to move to the selector arrow 34 the formula for which tolerances are to be entered. The software-controlled key 24 labeled PICK is pressed to select the formula. A checkmark (✓) 36 is placed to the right of the picked formula.

The software-controlled key 24 labeled TAB is pressed to move the selector arrow to the color difference parameters selection box. The software-controlled keys 24 labeled up arrow (↑) or down arrow (↓) are pressed to point the selector arrow 34 to the specific color difference parameter for which a tolerance value is to be entered. The software-controlled key 24 labeled PICK is pressed to pick that parameter. Tolerances are set a symmetrical plus-or-minus offsets from the standard that are acceptable.

With the selector box 38 in the numerical entry area of the display shown in FIG. 10E, the software-controlled key 24 labeled down arrow ($\downarrow$) is pressed to move the selector box vertically, or the software-controlled key 24 labeled right arrow ($\rightarrow$) is pressed to move the selector box horizontally, until the first digit of the tolerance to be entered is selected. The software-controlled key 24 labeled ENTER is pressed to enter the digit. If a mistake is made the software-controlled key 24 labeled BACK may be pressed to delete characters entered one at a time. The first digit of the tolerance appears on the screen in the parameter row have selected. This procedure is repeated to enter the remaining digits of the tolerance.

To enter the decimal point ($\bullet$), the $\bullet$ must be selected and the software-controlled key 24 labeled ENTER pressed. When the tolerance is properly displayed for the selected color difference parameter, the FINISH characters are selected and the software-controlled key 24 labeled ENTER is pressed. This procedure is then repeated for additional parameters. The escape key 22 is pressed to return to the standards management menu shown in FIG. 10B.

With the standards management menu displayed as shown in FIG. 10B, a single or a series of standards may be selected by pressing the software-controlled key 24 labeled up arrow ($\uparrow$) or down arrow ($\downarrow$) to point the selector arrow 34 to a specific standard. When the end of the list is reached, the selector arrow 34 cycles back to the beginning of the list. The software-controlled key 24 labeled PICK is pressed to either select (indicated by a check mark to the right of the selector arrow 34) or deselect (indicated by a blank space to the left of the standard). The software-controlled key 24 labeled PICK toggles between select and deselect. This means that once a standard is selected, pressing the software-controlled key 24 labeled PICK again deselects the same STANDARD.

To select all of the standards, the software-controlled key 24 labeled ALL is pressed. The portable spectrophotometer responds by placing a check mark to the right of ALL STANDARDS displayed on the display screen 16. To deselect all of the standards, the software-controlled key 24 labeled ALL is again pressed. The portable spectrophotometer responds by removing check marks to the left of ALL STANDARDS displayed on the display screen 16.

To activate a standard, the standard(s) to be activated is selected with the selector arrow 34 and the software-controlled key 24 labeled PICK as previously described. The menu key 20 is pressed to display the secondary standards management menu on the display screen 16 as shown in FIG. 10C. The software-controlled key 24 labeled ACTV is pressed to activate the standard(s) selected and an asterisk (*) appears next to the standard(s) activated. The software-controlled key 24 labeled ACTV toggles between activate and deactivate. This means that once a standard is activated, pressing the software-controlled key 24 labeled ACTV again deactivates the same standard.

To delete a standard, the standard(s) to be deleted are selected with the selector arrow 34 and the software-controlled key 24 labeled PICK as previously described. The menu key 20 is pressed to display the secondary standards management menu on the display screen 16 as shown FIG. 10C. The software-controlled key 24 labeled DEL is pressed to delete the standard(s) selected.

A trial is edited or viewed in the same manner as editing or viewing a standard with one exception: Tolerances cannot be entered for a trial. A trial is picked in the same manner as picking a standard. To make a trial into a standard, using the software-controlled key 24 labeled PICK as previously described, the trial to be made into a standard is selected. The software-controlled key 24 labeled STD is pressed and the trial is saved as a standard. The portable spectrophotometer returns to the trials management menu. A trial is deleted in the same manner as deleting a standard.

E. Setup Routine

Figure 11:
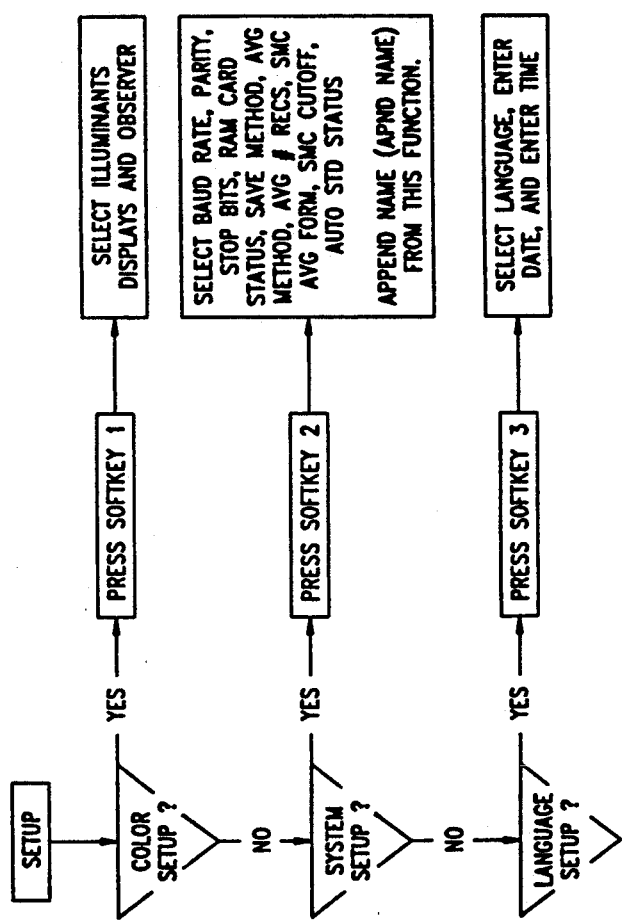
FIG. 11 is a flow diagram of the setup routine of the handheld portable spectrophotometer.

A flow diagram describing the setup routine of the portable spectrophotometer is set forth in FIG. 11 and described hereinafter. The color measurement parameters for the portable spectrophotometer that will be used routinely should be set prior to operation. This simplifies the color information that the portable spectrophotometer presents on display screens, and allows customization to specific applications. A set of default parameters may be automatically assigned for when the portable spectrophotometer is turned on for the very first time. The user may review these default parameters and set new ones at his option.

With the main menu displayed as shown in FIG. 4, software-controlled key 24 labeled 4 (SETUP) is pressed. With the setup menu displayed as shown in FIG. 12A, software-controlled key 24 labeled 1 (COLOR SETUP) is pressed to enter the color setup mode. Software-controlled key 24 labeled 2 (SYSTEM SETUP) is pressed to enter the system setup mode. Software-controlled key 24 labeled 3 (LANGUAGE) is pressed to enter the language mode. Software-controlled key 24 labeled 4 (DIAGNOSTICS) is pressed to enter the diagnostics mode.

Each of the setup modes may be selected and changed to customize the portable spectrophotometer to a specific application as follows. If the portable spectrophotometer has not been set up to display the user's native language, this setup should be performed first, then proceeding with the color setup and system setup.

The color setup option permits selection of illuminants, types of measurement display screens, and degree observer desired. With the setup menu displayed as shown in FIG. 12A, software-controlled key 24 labeled 1 (COLOR SETUP) is pressed to obtain the display screen shown in FIG. 12B. The software-controlled key 24 labeled up arrow ($\uparrow$) or down arrow ($\downarrow$) locates selector arrow 34 to point to a specific illuminant. When the end of the list is reached, the selector arrow 34 cycles back to the beginning of the list. The software-controlled key 24 labeled PICK is pressed to either activate (indicated by a check mark 36 to the right of the selector arrow 34) or deactivate (indicated by blank space to the right of the selector arrow) each illuminant.

Once one item in the list has been deactivated, as many items as desired can be sequentially turned off by pressing and holding down the software-controlled key 24 labeled PICK. The software-controlled key 24 labeled PICK is simply released to stop this deactivation.

The software-controlled key 24 labeled TAB may be pressed to move the selector arrow 34 to the display selection box. The software-controlled key 24 labeled up arrow (↑) or down arrow (↓) is pressed to point the selector arrow 34 to a specific display type. When the end of the list is reached, the selector arrow 34 cycles back to the beginning of the list.

The software-controlled key 24 labeled PICK is pressed to either activate (indicated by a check mark 36 to the right of the selector arrow 34) or deactivate (indicated by blank space to the right of the selector arrow 34) each display type to be seen. The software-controlled key 24 labeled TAB may be pressed to move the selector arrow 34 to the observer selection box. The software-controlled key 24 labeled PICK toggles between a 2° and a 10° observer for selection of the desired observer.

Figure 12C:
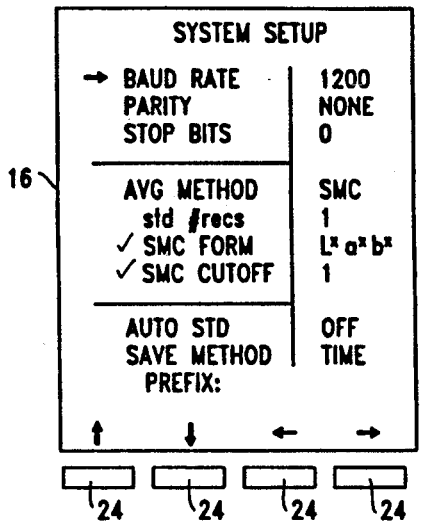

For system setup, with the setup menu displayed as shown in FIG. 12A, software-controlled key 24 labeled 2 (SYSTEM SETUP) is pressed to obtain the display screen shown in FIG. 12C. The first three items on the system setup display screen, baud rate, parity, and stop bits, facilitate the output of data through the DB9 connector 30. Each setting may be matched to the device that will receive the data transmission. If data will not be output, the first three system setup parameters may be ignored; any value assigned to them will be acceptable.

The software-controlled key 24 labeled up arrow (↑) or down arrow (↓) is pressed to move the selector arrow 34 to point to a specific parameter to be changed. The prefix parameter may only be accessed when the save method is set to APND. Active parameters may appear in capitalized letters.

With the selector arrow 34 to the left of BAUD RATE, if the displayed baud rate is to be changed to a different value, the software-controlled key 24 labeled right arrow (→) or left arrow (←) is pressed to display the desired baud rate. The possible selections for baud rate include 1200, 2400, 4800, 9600 and 19200. With the selector arrow 34 to the left of PARITY, the software-controlled key 24 labeled right arrow (→) or left arrow (←) is pressed to display the desired parity. The possible selections for parity are none, odd and even. With the selector arrow 34 to the left of STOP BITS, the software-controlled keys 24 labeled right arrow (→) or left arrow (←) is pressed to display the desired stop bits. The possible selections for stop bits include 0, 1 and 2. With the selector arrow 34 to the left of AVG METHOD, the software-controlled key 24 labeled right arrow (→) or left arrow (←) is pressed to display the desired averaging method status. The possible selections for averaging method status include standard, none and SMC.

When set to standard, the portable spectrophotometer has a user-definable number of measurement repetitions to average. Set to none, there is no sample averaging. Set to SMC (Statistical Measurement Control), the portable spectrophotometer automatically determines the number of measurements (ranging from 5-50) required to reduce or eliminate the effects of sample nonuniformity, positioning accuracy and within-instrument repeatability.

When standard is selected as the averaging method, the selector arrow 34 is moved to the left of the std #recs (average number of records to average). The software-controlled key 24 located right arrow (→) or left arrow (←) is pressed so that the desired number of records is displayed. Std #recs may be from 1 to 25.

When SMC is selected as the averaging method, the selector arrow 34 is moved to the left of SMC FORM (to indicate the formula that to be active when SMC mode is selected as the averaging method). The software-controlled key 24 labeled right arrow (→) or left arrow (←) is pressed to display the desired color difference formula. The possible selections for the SMC color difference formula include FMC, L*a*b*, L*C*h* and Lab.

The color difference formulas commonly used in color science are implemented as part of the portable spectrophotometer and are briefly explained herein. The abbreviations used in the portable spectrophotometer hardware and software follow standard conventions:

CIELAB—Also L*a*b*, CIELAB (Commission International de l'Eclairage) is the most commonly used color difference equation worldwide. It was issued in 1976 as an "improved" cube root equation. In this coordinate system L* is a measure of the lightness of the sample, ranging from 0 (black) to 100 (white). The quantities a* and b*, called opponent type coordinates, define the degree of its yellowness (positive b*), redness (positive a*) or greenness (negative a*), and blueness (negative b*). These coordinates approach zero for neutral colors (white, greys, black). As the values of a* and b* rise, the color becomes more chromatic or saturated.

L,a,b—Originally designed to be used with tristimulus colorimeters, the L,a,b, (Lab) equation is also known as Hunter Lab. It was first released in 1948 and later revised in 1958. In this coordinate system, L is a measure of the lightness of the sample, ranging from 0 (black) to 100 (white). The quantities a and b, called opponent type coordinates, indicate the degree of redness (positive a), greenness (negative a) and the degree of yellowness (positive b), blueness (negative b). These coordinates approach zero for neutral colors (white, greys, black). The higher the values of a and b, the more saturated or chromatic the color.

CIE XYZ, xy—In this coordinate system the CIE tristimulus values X, Y, Z and chromaticity coordinates x, y are used. X, Y, Z have been used since 1931 as the basic numerical description of color from which all other scales are derived. They represent the magnitudes of three stimuli derived from experiments determining the quantities of three colored lights needed to match the test stimulus or color. The tristimulus value Y is a direct measure of the lightness of surface colors on a (visually nonlinear) scale of 0 (black) to 100 (white). Values of X and Z are set relative to Y=100 for white by normalization. However, the maximum values of X and Z are not 100 but depend on the illuminant and standard observer data used. Chromaticity coordinates x and y are color coordinates which locate a color within color space.

$LCh_{ab}$ (referred to as LCH or LCh herein)—In this coordinate system, L is a measure of the lightness of the sample, ranging from 0 (black) to 100 (white). C is a measure of the sample's chroma. The higher the value of C, the more chromatic is the color. $h_{ab}$ is a measure of the sample's hue. The $h_{ab}$ values between 0° and 90° represent hues ranging from red (0°) to yellow (90°). $h_{ab}$ values between 90° and 180° represent hues ranging from yellow (90°) to green (180°). The $h_{ab}$ values between 180° and 270° represent hues ranging from green (180°) to blue (270°). The $h_{ab}$ values between 270° and 360° represent hues ranging from blue (270°) to red (360°).

FMC-II (also referred to as FMC-2 and FMC2—The Friele-MacAdam-Chickering equations (1967 and 1971) were a collaborative effort of the individuals for whom the equations have been named. Both FMC-I and FMC-II equations have undergone a series of refinements and improvements since their introduction.

When SMC is selected as the averaging method, the selector arrow 34 is moved to the left of the SMC CUTOFF (to indicate the cutoff value to be active when SMC mode is selected as the averaging method). The software-controlled key 24 labeled right arrow (→) or left arrow (←) is pressed so to display the desired SMC cutoff value. The SMC cutoff may range from 1 to 25.

The value assigned to SMC cutoff depends on the color difference formula chosen to be active in the SMC mode. The cutoff value is the average error allowed for measurements included in the average. If this error is not met, the portable spectrophotometer will require additional readings until such time as the error level is met.

With the selector arrow to the left of AUTO STD, the software-controlled key 24 labeled right arrow (→) or left arrow (←) is pressed to display the desired status of this option. The auto standard may be set either off or on.

With AUTO STD set on, the portable spectrophotometer will automatically select the active standard color that is closest in color (lowest ▲ E) to a measured trial. With this capability, the five standards closest to the measured trial maybe viewed. Standards are selected beginning with the lowest ▲ E and ending with the highest ▲ E. Set to off, this option is inactive.

With the selector arrow to the left of SAVE METHOD, the software-controlled key 24 labeled right arrow (→) or left arrow (←) is pressed to display the save method status. When set to APND, a sequential prefix may be added to each standard with a series of up to 8 alphanumeric characters. Set to TIME, the portable spectrophotometer produces default names based upon a time stamp. Set to STD, the portable spectrophotometer adds sequential numbers to the activity standard name. Set to FULL, the portable spectrophotometer displays the record identifier editing screen whenever a standard is saved.

Figure 12D:
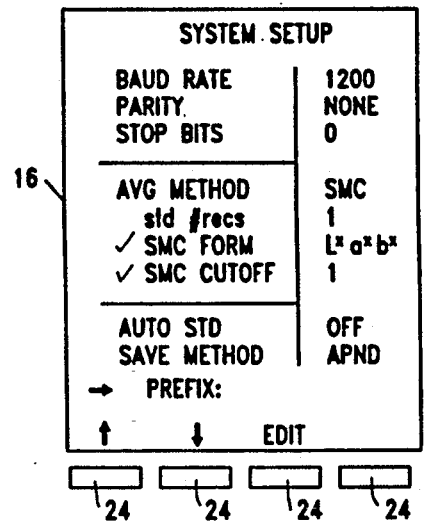

The system setup enables the user to enter the prefix that will be added to each standard in the append mode. After selecting the append mode, the selector arrow is moved to the left of PREFIX. Software-controlled key 24 labeled EDIT as shown in FIG. 12D is pressed and the display screen displays the alphanumeric selector screen as shown in FIG. 10D. The alphanumeric selector screen contains a 64-character keyboard having eight columns and eight rows. The word FINISHED is selected when the entry is complete. A desired character is selected using the software-controlled key 24 labeled up arrow (↑) in a vertical column and the software-controlled key 24 labeled right arrow (→) in a horizontal row. The uppermost left character is blank, and is selected to place a space in an entry.

As an example, the old name is COAL BLACK as shown in FIG. 10D is to be changed to a new name called DEMO. The software-controlled key 24 labeled BACK is pressed to delete the last character entered. The software-controlled key 24 labeled ENTR is pressed to select a character. The software-controlled key 24 labeled down arrow (↓) is pressed once to move the selection box 38 from FINISHED to the uppermost left corner of the menu (the blank space character).

To enter the word DEMO, the software-controlled key 24 labeled (↓) down arrow is pressed 4 times until the letter @ appears in the selection box. The letter D appears in this fifth row of characters. The software-controlled key 24 labeled right arrow (→) is pressed 4 times until the letter D appears in the selection box. The software-controlled key 24 labeled ENTR is pressed to select the D. The letter D then appears next to the word NEW: on the display screen. The software-controlled key 24 labeled right arrow (→) is pressed once until the letter E appears in the selection box 38. The software-controlled key 24 labeled ENTR is pressed to select the E. The software-controlled key 24 labeled down arrow (↓) is pressed once until the letter M appears in the selection box. The software-controlled key 24 labeled ENTR is pressed to select the M. The software-controlled key 24 labeled right arrow (→) is pressed two times until the letter O appears in the selection box 38. The software-controlled key 24 labeled ENTR is pressed to select the O. The software-controlled key 24 labeled down arrow (↓) is pressed three times until the selection box 38 is moved to FINISHED. The software-controlled key 24 labeled ENTR is pressed to complete the entry of the new name.

Figure 12E:
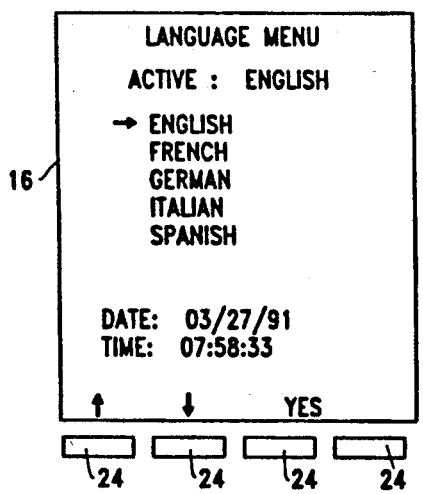

To access language mode, with the setup menu displayed as shown in FIG. 12A, software-controlled key 24 labeled 3 (LANGUAGE) is pressed to obtain the display shown in FIG. 12E. The software-controlled key 24 labeled up arrow (↑) or down arrow (↓) is pressed to move the selector arrow 34 to point to a specific language to be selected. The software-controlled key 24 labeled YES is pressed to select the language. The language menu and all other labels will now appear in the language chosen.

Figure 12F:
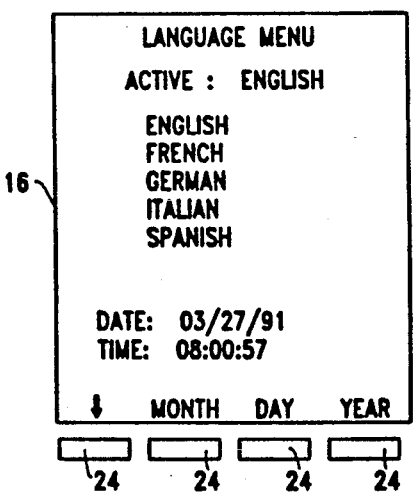

After pressing the menu key 20 to obtain the display screen shown in FIG. 12F, the up arrow (↑) displayed above the first software-controlled key 24 indicates that when pressing the software-controlled key 24 labeled MONTH, DAY or YEAR, the displayed value will increase. To decrease these values, press the software-controlled key 24 labeled up arrow (↑) and the label will change to a down arrow (↓), indicating that when the software-controlled key 24 labeled MONTH, DAY or YEAR is pressed, the displayed value will decrease. The date may be set accordingly.

Figure 12G:
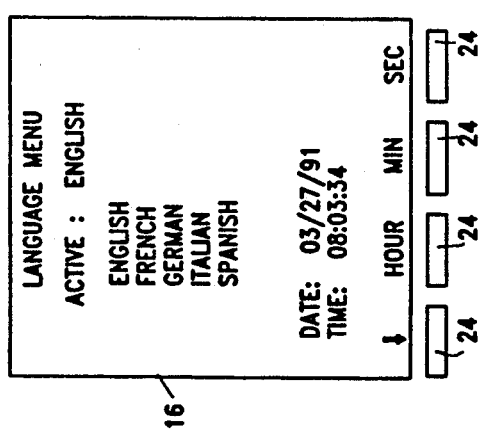

After pressing the menu key 20 to obtain the display screen shown in FIG. 12G, the up arrow (↑) displayed above first software-controlled key 24 indicates that pressing the software-controlled key 24 labeled HOUR, MIN, or SEC, will increase the displayed values. To decrease these values, the software-controlled key 24 labeled up arrow (↑) is pressed and the label will change to an down arrow (↓), indicating that when pressing the software-controlled key 24 labeled HOUR, MIN or SEC, the displayed value will decrease.

F. Sample Measurement Screens

Figure 13:
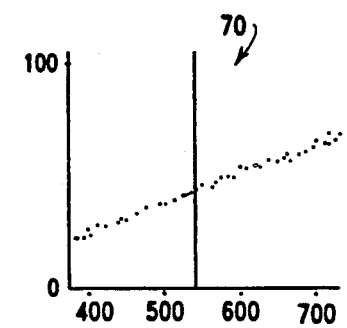
FIG. 13 is a percent reflectance plot displayed by the handheld portable spectrophotometer.

A percent reflectance plot in accordance with the invention is shown in FIG. 13. The percent reflectance plot 70 is a rectilinear display of wavelength (horizontally) versus percent reflectance (vertically). The wavelength of the visible range is presented in nanometers. The scale of the percent reflectance plot is a full ±100% range. The standard displayed 72 is indicated as well as the percent reflectance at particular wavelengths 74.

Figure 14:
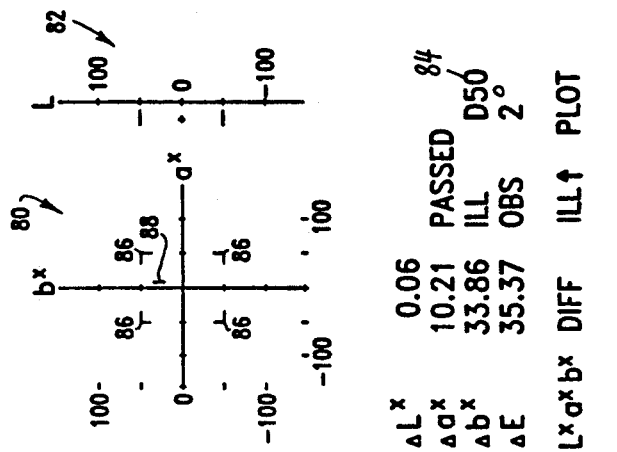
FIG. 14 is a color plot displayed by the handheld portable spectrophotometer.

A color plot in accordance with the invention is shown in FIG. 14. The color plot shows the coordinates of the trial relative to those of the standard. The scale of the color plot is set at a fully ±100 range.

The color plot 80 is a rectilinear display of redness/greenness (horizontally) versus yellowness/blueness (vertically). The coordinates of the standard are located at the center (zero point) of the vertical and horizontal axes. The coordinates of the trial are located at the crosshairs (+).

To the right side of the color plot is a vertical scale 82, illustrating the lightness/darkness of the trial in relation to that of the standard. The lightness/darkness of the standard is at the center (zero point) of the scale. The lightness/darkness of the trial is illustrated by a crosshairs (+) on the vertical axis.

The illuminant 84 shown is encoded in the same format as was selected in the setup. In FIG. 14, the color plot is shown for a D50 illuminant.

The boundaries of the "in tolerance" or the "passed" condition and "out of tolerance" or "failed" condition are displayed by markers 86 that indicate the corners of a square. A crosshairs 88 outside this square is out of tolerance, while a crosshairs within the square is within tolerance.

G. Computer Interface

The portable spectrophotometer in accordance with the invention is particularly adapted for use in combination with a personal computer. This combination provides full computing power for maintaining and evaluating color data standards and trial tests results along with complete portability for trial test measurement.

The portable spectrophotometer can store approximately 200 color standards and test readings (not including data stored in RAM card 26). In combination with the personal computer software, however, the number of standards and test readings that can be stored is limited only by the disk space available on the personal computer.

In a typical application, the personal computer transfers a set of color standards to the portable spectrophotometer. The portable spectrophotometer measures product samples using these standards as color targets. The portable spectrophotometer also stores the results of those trial test measurements.

If required for quality assurance, trial test results can be transferred to the personal computer for storage. Such stored files then can be used by any external statistics or analysis software package adapted to read dBase III (a product of Ashton Tate) formatted files.

The personal computer and related software may also be used to maintain data and to transmit data between the personal computer and the portable spectrophotometer. There are three aspects to this function: maintaining the database, sending color standards to the portable spectrophotometer, and receiving measurements from the portable spectrophotometer.

As a database manager, the personal computer software allows the user to group color standards into logical files. Each of these files contains as many records as needed. A user is free to assign his own names and codes to individual color standards, including duplicate names or codes.

Each color standard may define the color space with 38 points of reflectance data, ranging from 380 nm to 750 nm. For trial test measurements, each color standard may define the tolerances for color difference values. For example, in the LCh scale, each standard may define the maximum and minimum variances in luminance (DL), color (DC), hue (Dh), and combined score (DE) for 3 illuminants.

As a database manager, the personal computer software allows a user to do the following:
Edit records;
Sort records by name or code;
Search for records by name or code;
Select records for transmission or deletion;
Create new data files; and
Print all data for selected records.

Transmission of data between the portable spectrophotometer and the personal computer may be controlled by the personal computer software.

Before test trial measurements are taken with the portable spectrophotometer, the color standards to be used may be selected and sent from the personal computer's database. Similarly, reflectance data for new colors or for test trial measurements may be stored in the portable spectrophotometer and then received by the personal computer to be added to the database.

All data files may be stored in the format standardized by dBase III. This format is widely compatible with other personal computer software packages. As a result, data can be transferred from the personal computer software to any program adapted to work with dBase II files.

A typical example of such data transfer involves statistical analysis of test trial measurements. The personal computer software may store such measurements in separate files on the personal computer. Those files are then available to standard statistical programs for analysis and reporting.

While the invention has been described in its preferred embodiment, it is to be understood that the words which have been used are words of description, rather than limitation, and that changes may be made within the purview of the appended claims without departing from the true scope and the spirit of the invention in its broader aspects.

For example, the portable spectrophotometer described herein also has the capability to make radiometric and transmissive measurements. Unlike a spectrophotometer, which utilizes an illuminator and analyzes the light reflected from an illuminated sample, a radiometer analyzes the light emanating from a source.

Radiometric measurements may be accomplished by disabling the illumination flash so that light may enter the portable spectrophotometer and adjusting the integration time so that the portable spectrophotometer operates in the proper dynamic range. Calibration can be done on a known light source and dark measurement can be performed by blocking all light entering the instrument.

Sources of illumination that are typically measured are: 1) CRT displays; 2) L.E.D.'s; and 3) lighting products (i.e., incandescent and fluorescent lights).

Information that may be obtained by a radiometric measurement includes 1) spectral power distribution—the amount of energy produced by the source at each wavelength; 2) chromaticity coordinates; 3) tristimulus values; and 4) color temperature. All of these parameters are widely used by industry.

Transmissive measurements may be accomplished by placing a white standard in the sample plane of the portable spectrophotometer and placing a sample into the optical pickup path, typically in front of the pickup lens. By placement of a sample in the optical path of the portable spectrophotometer, a measurement of the transmissive properties of the sample may be obtained.

What is claimed:

1. A handheld portable spectrophotometer, comprising:
   keys for input of instructions by a user;
   an illuminator for illuminating a sample;
   a spectral analyzer for separating light reflected from said sample into spectral components and producing a signal corresponding to the level of each spectral component;
   a processor for executing said instructions and performing color matching based on an analysis of said signal;
   a display for displaying the results of said color matching; and
   a power source for providing power for operation of the handheld portable spectrophotometer.

2. A handheld portable spectrophotometer in accordance with claim 1, wherein the illuminator is within a housing non-coextensive with a housing containing the processor.

3. A handheld portable spectrophotometer in accordance with claim 1, further comprising a replaceable memory.

4. A handheld portable spectrophotometer in accordance with claim 3, wherein said replaceable memory contains color standards data.

5. A handheld portable spectrophotometer in accordance with claim 1, further including an adapter to allow the portable spectrophotometer to communicate with external devices.

6. A handheld portable spectrophotometer in accordance with claim 1, wherein said processor applies user-selected color difference formulas in the analysis of said signal.

7. A handheld portable spectrophotometer in accordance with claim 1, wherein said processor provides a facility to compare the results of said analysis with color standards data.

8. A handheld portable spectrophotometer in accordance with claim 1, wherein said processor includes a facility for the user to manipulate data stored in the handheld portable spectrophotometer.

9. A handheld portable spectrophotometer in accordance with claim 1, wherein said display is a graphics display.

10. A handheld portable spectrophotometer in accordance with claim 1, wherein said spectral analyzer is adapted to compensate for thermal changes.

11. A handheld portable spectrophotometer in accordance with claim 10, wherein optical components of said spectral analyzer are secured in place and a circuit board of said spectral analyzer is mounted to allow movement thereof to correct for thermal expansion of said circuit board.

12. A handheld portable spectrophotometer in accordance with claim 1, wherein said spectral analyzer is mechanically isolated against shock and vibration.

13. A handheld portable spectrophotometer in accordance with claim 12 wherein optical components of said spectral analyzer are secured in place and said spectral analyzer is mounted on a mechanically-isolating support.

14. A handheld portable spectrophotometer, comprising:
   means for input of instructions by a user;
   means for illuminating a sample;
   means for separating light reflected from said sample into spectral components and producing a signal corresponding to the level of each spectral component;
   means for executing said instructions and for performing color matching based on an analysis of said signal;
   means for displaying the results of said color matching; and
   means for providing power for operation of the handheld portable spectrophotometer.

15. A handheld portable spectrophotometer in accordance with claim 14, wherein the means for illuminating is within a housing non-coextensive with a housing containing the means for executing said instructions and for analyzing said signal.

16. A handheld portable spectrophotometer in accordance with claim 14, further comprising a replaceable means for data storage.

17. A handheld portable spectrophotometer in accordance with claim 16, wherein said replaceable means for data storage contains color standards data.

18. A handheld portable spectrophotometer in accordance with claim 14, further including means for facilitating communication of the handheld portable spectrophotometer with external devices.

19. A handheld portable spectrophotometer in accordance with claim 14, wherein said means for executing said instructions and for analyzing said signal further includes means for applying user-selected color difference formulas in the analysis of said signal.

20. A handheld portable spectrophotometer in accordance with claim 14, further comprising means for manipulating data stored in the handheld portable spectrophotometer.

21. A handheld, portable spectrophotometer in accordance with claim 14, further comprising means for graphically displaying the results of the analysis of said signal.

22. A handheld portable spectrophotometer in accordance with claim 14, further comprising means to compare the results of the analysis of said signal with color standards data.

23. A handheld portable spectrophotometer, comprising:
   keys for input of instructions by a user;
   an illuminator for illuminating a sample;
   a spectral analyzer for separating light reflected from said sample into spectral components and producing a signal corresponding to the level of each spectral component;
   a processor for executing said instructions and analyzing said signal;
   a display for displaying the results of said signal analysis; and
   a power source for providing power for operation of the handheld portable spectrophotometer.
   wherein the illuminator is within a housing non-coextensive with a housing containing the processor.

24. A handheld portable spectrophotometer in accordance with claim 23, further comprising a user-replaceable memory.

25. A handheld portable spectrophotometer in accordance with claim 24, wherein said user-replaceable memory contains color standards data.

26. A handheld portable spectrophotometer in accordance with claim 24, wherein said user-replaceable memory contains application program instructions.

27. A handheld portable spectrophotometer in accordance with claim 23, further including an adapter to allow the portable spectrophotometer to communicate with external devices.

28. A handheld portable spectrophotometer in accordance with claim 23, wherein said processor applies user-selected color difference formulas in the analysis of said signal.

29. A handheld portable spectrophotometer in accordance with claim 23, wherein said processor provides a facility to compare the results of said analysis with color standards data.

30. A handheld portable spectrophotometer in accordance with claim 23, wherein said processor includes a facility for the user to manipulate data stored in the handheld portable spectrophotometer.

31. A handheld portable spectrophotometer in accordance with claim 23, wherein said spectral analyzer is adapted to compensate for thermal changes.

32. A handheld portable spectrophotometer in accordance with claim 31, wherein optical components of said spectral analyzer are secured in place and a circuit board of said spectral analyzer is mounted to allow movement thereof correct for thermal expansion of said circuit board.

33. A handheld portable spectrophotometer in accordance with claim 23, wherein said spectral analyzer is mechanically isolated against shock and vibration.

34. A handheld portable spectrophotometer in accordance with claim 33, wherein optical components of said spectral analyzer are secured in place and said spectral analyzer is mounted on a mechanically-isolating support.

35. A handheld portable spectrophotometer, comprising:
   keys for input of instructions by a user;
   an illuminator for illuminating a sample;
   a spectral analyzer for separating light reflected from said sample into spectral components and producing a signal corresponding to the level of each spectral component;
   a processor for executing said instructions and analyzing said signal;
   a user-replaceable memory containing information for use by said processor in said signal analysis;
   a display for displaying the results of said signal analysis; and
   a power source for providing power for operation of the handheld portable spectrophotometer.

36. A handheld portable spectrophotometer in accordance with claim 35, wherein the illuminator is within a housing non-coextensive with a housing containing the processor.

37. A handheld portable spectrophotometer in accordance with claim 35, wherein the information in said user-replaceable memory is color standards data.

38. A handheld portable spectrophotometer in accordance with claim 35, wherein the information in said user-replaceable memory is application program instructions.

39. A handheld portable spectrophotometer in accordance with claim 35, further including an adapter to allow the portable spectrophotometer to communicate with external devices.

40. A handheld portable spectrophotometer in accordance with claim 35, wherein said processor applies user-selected color difference formulas in the analysis of said signal.

41. A handheld portable spectrophotometer in accordance with claim 35, wherein said processor provides a facility to compare the results of said analysis with color standards data.

42. A handheld portable spectrophotometer in accordance with claim 35, wherein said processor includes a facility for the use to manipulate data stored in the handheld portable spectrophotometer.

43. A handheld portable spectrophotometer in accordance with claim 35, wherein said spectral analyzer is adapted to compensate for thermal changes.

44. A handheld portable spectrophotometer in accordance with claim wherein optical components of said spectral analyzer are secured in place and a circuit board of said spectral analyzer is mounted to allow movement thereof to correct for thermal expansion of said circuit board.

45. A handheld portable spectrophotometer in accordance with claim 35, wherein said spectral analyzer is mechanically isolated against shock vibration.

46. A handheld portable spectrophotometer in accordance with claim 45, wherein optical components of said spectral analyzer are secured in place and said spectral analyzer is mounted on a mechanically-isolating support.

47. A handheld portable spectrophotometric, radiometric and transmissive measurement apparatus comprising:
   keys for input of instructions by a user;
   an illuminator for illuminating a sample;
   means for enabling and disabling operation of said illuminator in response to said instructions;
   a spectral analyzer for separating light reflected and emanated from said sample into spectral components and producing a signal corresponding to the level of each spectral component;
   a processor for executing said instructions and and analyzing said signal;
   a display for displaying the results of said signal analysis; and
   a power source for providing power for operation of the handheld portable spectrophotometer.

48. A handheld portable spectrophotometric, radiometric and transmissive measurement apparatus in accordance with claim 47, further including an adapter to allow the measurement apparatus to communicate with external devices.

49. A handheld portable spectrophotometric, radiometric and transmissive measurement apparatus in accordance with claim 47, wherein said processor applies user-selected color difference formulas in the analysis of said signal.

50. A handheld portable spectrophotometric, radiometric and transmissive measurement apparatus in accordance with claim 47, wherein said processor provides a facility to compare the results of said analysis with color standards data.

51. A handheld portable spectrophotometric, radiometric and transmissive measurement apparatus in accordance with claim 47, wherein said processor includes a facility for the user to manipulate data stored in the measurement apparatus.

52. A handheld portable spectrophotometric, radiometric and transmissive measurement apparatus in accordance with claim 47, wherein said spectral analyzer is adapted to compensate for thermal changes.

53. A handheld portable spectrophotometric, radiometric and transmissive measurement apparatus in accordance with claim 52, wherein optical components of said spectral analyzer are secured in place and a circuit board in said spectral analyzer is mounted to allow movement thereof to correct for thermal expansion of said circuit board.

54. A handheld portable spectrophotometric, radiometric and transmissive measurement apparatus in accordance with claim 47, wherein said spectral analyzer is mechanically isolated against shock and vibration.

55. A handheld portable spectrophotometric, radiometric and transmissive measurement apparatus in accordance with claim 54, wherein optical components of said spectral analyzer are secured in place and said spectral analyzer is mounted on a mechanically-isolating support.

56. A handheld portable spectrophotometric, radiometric and transmissive measurement apparatus comprising:
keys for input of instructions by a user;
an illuminator for illuminating a sample;
a spectral analyzer for separating light reflected or emanated from said sample into spectral components and producing a signal corresponding to the level of each spectral component;
a processor for executing said instructions and and analyzing said signal;
a display for displaying the results of said signal analysis;
a power source for providing power for operation of the handheld portable spectrophotometer; and
wherein the illuminator is within a housing non-coextensive with a housing containing the processor.

57. A handheld portable spectrophotometric, radiometric and transmissive measurement apparatus comprising:
keys for input of instructions by a user;
an illuminator for illuminating a sample;
a spectral analyzer for separating light reflected or emanated from said sample into spectral components and producing a signal corresponding to the level of each spectral component;
a processor for executing said instructions and and analyzing said signal;
a display for displaying the results of said signal analysis;
a power source for providing power for operation of the handheld portable spectrophotometer.
a replaceable memory.

58. A handheld portable spectrophotometric, radiometric and transmissive measurement apparatus in accordance with claim 57, wherein said replaceable memory contains color standards data.

59. A handheld portable spectrophotometric, radiometric and transmissive measurement apparatus in accordance with claim 57, wherein said replaceable memory contains application program instructions.

* * * * *